US006306177B1

(12) United States Patent
Felt et al.

(10) Patent No.: US 6,306,177 B1
(45) Date of Patent: *Oct. 23, 2001

(54) BIOMATERIAL SYSTEM FOR IN SITU TISSUE REPAIR

(75) Inventors: Jeffrey C. Felt, Greenwood; Mark A. Rydell, Golden Valley; Richard J. Zdrahala, Eden Prairie; Alexander Arsenyev, Eagan, all of MN (US)

(73) Assignee: Advanced Bio Surfaces, Inc., Minnetonka, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/993,468

(22) Filed: Dec. 18, 1997

Related U.S. Application Data

(63) Continuation of application No. PCT/US97/20874, filed on Nov. 14, 1997, and a continuation-in-part of application No. 08/749,429, filed on Nov. 15, 1996, now abandoned, which is a continuation-in-part of application No. 08/742,444, filed on Nov. 2, 1996, now Pat. No. 5,795,353, which is a continuation of application No. 08/474,113, filed on Jun. 7, 1995, now abandoned, which is a division of application No. 08/239,248, filed on May 6, 1994, now Pat. No. 5,556,429, application No. 08/993,468, which is a continuation-in-part of application No. 08/903,455, filed on Jul. 30, 1997, now abandoned, which is a continuation-in-part of application No. 08/590,293, filed on Jan. 23, 1996, now Pat. No. 5,888,220.
(60) Provisional application No. 60/056,624, filed on Aug. 20, 1997.

(51) Int. Cl.⁷ ...................................................... A61F 2/30
(52) U.S. Cl. ........................................ 623/23.6; 623/18.11
(58) Field of Search .................................. 623/11, 16, 18, 623/66, 901, 18.11; 128/898; 433/223, 226

(56) References Cited

U.S. PATENT DOCUMENTS

| | | |
|---|---|---|
| 3,030,951 | 4/1962 | Mandarino . |
| 3,875,595 | 4/1975 | Froning . |
| 4,098,626 | 7/1978 | Graham et al. . |
| 4,203,444 | 5/1980 | Bonnell et al. ....................... 128/276 |
| 4,368,040 | 1/1983 | Weissman . |
| 4,446,578 | 5/1984 | Perkins et al. . |
| 4,477,604 | 10/1984 | Oechsle, III .......................... 523/116 |
| 4,570,270 | 2/1986 | Oechsle, III . |
| 4,594,380 | 6/1986 | Chapin et al. . |
| 4,651,736 | 3/1987 | Sanders ................................ 128/305 |
| 4,722,948 | 2/1988 | Sanderson ............................. 523/115 |
| 4,743,632 | 5/1988 | Marinovic ............................. 523/118 |
| 4,863,477 | 9/1989 | Monson . |
| 4,880,610 | 11/1989 | Constantz ............................. 423/305 |
| 4,904,260 | 2/1990 | Ray et al. . |
| 4,913,701 | 4/1990 | Tower . |
| 4,932,969 | 6/1990 | Frey et al. . |
| 4,969,888 | 11/1990 | Scholten et al. ........................ 606/94 |
| 5,007,940 | 4/1991 | Berg ........................................ 623/66 |
| 5,067,964 | 11/1991 | Richmond et al. ..................... 623/18 |
| 5,082,803 | 1/1992 | Sumita ...................................... 501/1 |
| 5,108,404 | 4/1992 | Scholten et al. ........................ 606/94 |
| 5,109,077 | 4/1992 | Wick ..................................... 525/467 |
| 5,143,942 | 9/1992 | Brown .................................. 521/110 |

(List continued on next page.)

| | | |
|---|---|---|
| 5,156,777 | 10/1992 | Kaye . |

FOREIGN PATENT DOCUMENTS

| | | |
|---|---|---|
| 0 353 936 | 2/1990 | (EP) . |
| 0 505 634 | 9/1992 | (EP) . |
| 0 521 573 | 1/1993 | (EP) . |
| 2 639 823 | 6/1990 | (FR) . |
| WO 9311723 | 6/1993 | (WO) . |
| WO 9531946 | 11/1995 | (WO) . |
| WO 9531948 | 11/1995 | (WO) . |

OTHER PUBLICATIONS

Brauer and Antonucci, "Dental Applications", Concise Encyclopedia of Polymer Science and Engineering, pp. 257–258.

J. Brydson, ed., "Polyurethanes and Polyisocanurates", Chapter 27, Plastics Materials, 6th ed., Butterworth Heeinemann (1995).

Hill–West, et al., Obstet. Gynecol. 83(1):59–64 (1994) "Prevention of Postoperative Adhesion in the Rat by situ Polymerization of Bioresorbable Hydrogel Barriers".

Peppas et al., "New Challenges in Biomaterials", Science, 263:1715–1720 (1994).

Frederick H. Silver, edl, Chapter 1, Biomaterials, Medical Devices and Tissue Engineering: An Integrated Approach, Chapman and Hall, 1994.

Hergenrother et al., "Effect of hard segment chemistry and strain on the stability of polyurethanes; in vivo biostability", Biomaterials, 14: 449–458 (1993).

A. Takahara, et al., "Effect of Soft Segment Chemistry on the Biostability of Segmented Polyurethanes. I. In vitro Oxidation", J. Biomedical Materials Research, 25:341–356 (1991).

A. Takahara et al., "Effect of Soft Segment Chemistry on the Biostability of Segmented Polyurethanes. II. In vitro Hydrolytic Degradation and Lipid Sorption", J. Biomedical Materials Research, 26:801–818 (1992).

*Primary Examiner*—Bruce Snow
(74) *Attorney, Agent, or Firm*—Fredrikson & Byron, P.A.

(57) ABSTRACT

A method, and related composition and apparatus for repairing a tissue site. The method involves the use of a curable polyurethane biomaterial composition having a plurality of parts adapted to be mixed at the time of use in order to provide a flowable composition and to initiate cure. The flowable composition can be delivered using minimally invasive means to a tissue site and there fully cured provide a permanent and biocompatible prosthesis for repair of the tissue site. Further provided are a mold apparatus, e.g., in the form of a balloon or tubular cavity, for receiving a biomaterial composition, and a method for delivering and filling the mold apparatus with a curable composition in situ to provide a prosthesis for tissue repair.

24 Claims, 6 Drawing Sheets

U.S. PATENT DOCUMENTS

| | | |
|---|---|---|
| 5,166,115 | 11/1992 | Brown ................................. 521/110 |
| 5,171,280 | 12/1992 | Baumgartner . |
| 5,254,662 | 10/1993 | Szycher et al. ........................ 528/67 |
| 5,278,201 | 1/1994 | Dunn et al. ........................... 523/113 |
| 5,288,797 | 2/1994 | Khalil et al. .......................... 524/872 |
| 5,290,306 | 3/1994 | Trotta et al. . |
| 5,334,201 | 8/1994 | Cowan . |
| 5,342,305 | 8/1994 | Shonk . |
| 5,344,444 | 9/1994 | Glastra . |
| 5,411,477 | 5/1995 | Saab . |
| 5,458,643 | 10/1995 | Oka et al. . |
| 5,470,314 | 11/1995 | Walinsky . |
| 5,529,653 | 6/1996 | Glastra . |
| 5,545,229 | 8/1996 | Parsons et al. . |
| 5,549,679 | 8/1996 | Kuslich . |
| 5,556,429 | 9/1996 | Felt . |
| 5,562,736 | 10/1996 | Ray et al. .............................. 623/17 |
| 5,571,189 | 11/1996 | Kuslich . |
| 5,591,199 | 1/1997 | Porter et al. . |
| 5,624,463 | 4/1997 | Stone et al. ........................... 623/18 |

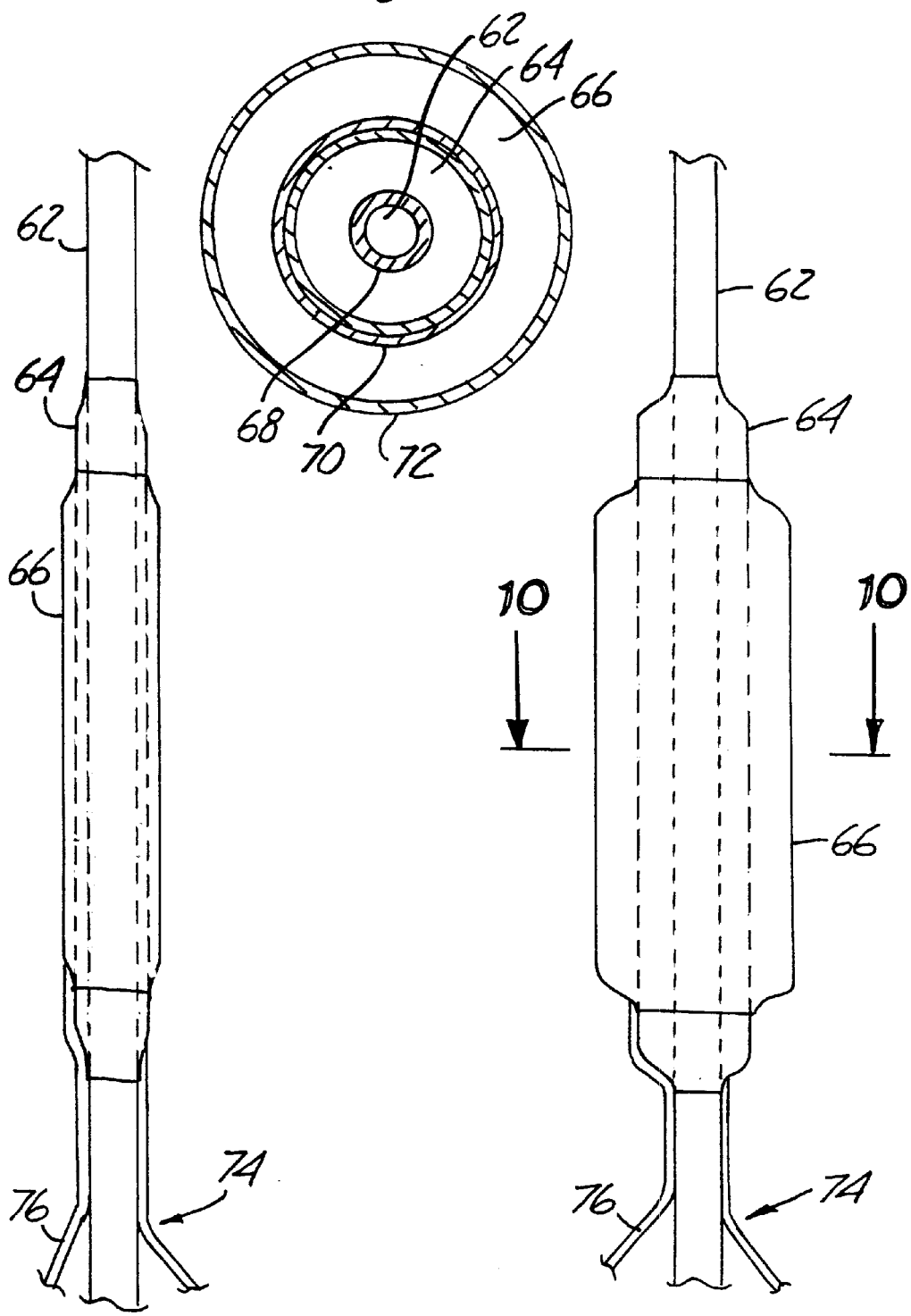

BIOMATERIAL SYSTEM FOR IN SITU TISSUE REPAIR

CROSS REFERENCE TO RELATED APPLICATIONS

This application is filed as a continuation application of International Patent Application Ser. No. PCT/US97/20874, filed Nov. 14, 1997 for BIOMATERIAL SYSTEM FOR IN SITU TISSUE REPAIR; and as a continuation-in-part of U.S. patent application Ser. No. 60/056,624, filed Aug. 20, 1997 for JOINT RESURFACING SYSTEM; and as a continuation-in-part of U.S. patent application Ser. No. 08/749,429, filed Nov. 15, 1996, now abandoned, for MINIMALLY INVASIVE RESURFACING SYSTEM, which is a continuation-in-part of application Ser. No. 08/742,444, filed on Nov. 2, 1996, issued Aug. 18, 1998 as U.S. Pat. No. 5,795,353, for JOINT RESURFACING SYSTEM, which is a File Wrapper Continuation of application Ser. No. 08/474,113 filed on Jun. 7, 1995, now abandoned, which is a divisional of prior application Ser. No. 08/239,248, filed on May 6, 1994, now U.S. Pat. No. 5,556,429, issued Sep. 17, 1996, for JOINT RESURFACING SYSTEM; and as a continuation-in-part of U.S. patent application Ser. No. 08/903,455, filed Jul. 30, 1997, now abandoned, which is a continuation-in-part of application Ser. No. 08/590,293, filed Jan. 23, 1996, issued Mar. 30, 1999 as U.S. Pat. No. 5,888,220 for ARTICULATING JOINT REPAIR.

TECHNICAL FIELD

The present invention relates to methods, apparatuses, materials and systems for the repair of musculoskeletal injury, and in particular, for bone and cartilage repair and replacement.

In another aspect, the invention relates to polymeric compositions, and to minimally invasive methods and materials for the preparation of prosthetic implants and the replacement or repair of joints and joint surfaces within the body. In another aspect the invention relates to in situ curable compositions, such as polymer compositions, useful for such purposes.

In yet another aspect, the present invention relates to medical prostheses for use in in vivo applications, to methods of preparing and delivering such prostheses, and to materials useful for fabricating or preparing prostheses. In a further aspect, the invention relates to the preparation of prostheses in situ.

BACKGROUND OF THE INVENTION

The musculoskeletal system is subject to injury caused by traumatic events as well as by a number of diseases, such as osteoarthritis and rheumatoid arthritis.

Repair of connective tissue of the musculoskeletal system is commonly performed using materials such as natural or synthetic tendons and ligaments. Joint repair and replacement is typically accomplished using metal and/or polymeric implants and devices. Such devices are typically fixated into existing bone by means of bone plates, adhesives, screws, and the like.

The joints of the body can be classified as between those that provide immovable articulations (synarthroidal), mixed articulations (amphiarthroidal), and movable articulations (diarthroidal). The ability of amphiarthroidal and diarthroidal joints to provide effective and pain-free articulation, and/or to serve their weight-bearing function, is generally dependent on the presence of intact, healthy cartilage (e.g., fibrocartilage or hyaline cartilage) within the joint.

Total joint replacement is indicated under conditions in which the cartilage surface between the bones forming a joint has degenerated. Often it has degenerated to a point where there is significant pain during locomotion, as well as during translation and rotation of joint components. Such degenerative joint disease is commonly treated by a technique known as total joint replacement arthroplasty, which is typically an invasive procedure that involves replacement of the original surfaces with artificial weight bearing materials in the form of implants.

Hip replacement generally involves the implantation of a femoral component in the form of a ball mounted on a shaft, together with an acetabular component in the form of a socket into which the ball sits.

Total knee replacement is somewhat more difficult than hip replacement because of the complex loading pattern of the knee. The tibial component of a total knee replacement is fixed in the cancellous bone of the tibia. The femoral component is typically fixed to the cortical bone of the femoral shaft using a suitable cement.

The tibial portion of a knee prosthetic device generally involves the insertion of a broad plateau region covering the tibia, after bone of the subchondral plate is removed. In most designs, a composite material is provided, involving a metal support underlying a polymeric, or fiber-reinforced polymeric tray.

A wide array of materials have been described for use in the manufacture of medical implants. See generally, Chapter 1, in *Biomaterials, Medical Devices and Tissue Engineering: An Integrated Approach*, Frederick H. Silver, ed., Chapman and Hall, 1994. Such materials generally fall into the categories of metals, polymers, ceramics, and composite materials.

A recent article entitled "New Challenges in Biomaterials", *Science*, 263:1715–1720 (1994), Peppas et al., provides a useful overview of the current state of the art in biomaterials. The article describes a number of materials currently used for orthopedic applications, including metals (iron, cobalt, and titanium), degradable polymers, self-reinforced compositions of polyglycolic acid, stronger polymers such as polydioxanone, and ceramic materials such as hydroxyapatite and certain glasses.

Elsewhere, for instance at page 1719, the Peppas et al. article refers to the potential usefulness of polymers that can be triggered to undergo a phase change. The article itself does not identify such polymers, but instead postulates that materials that are initially liquid might be administered through a minimally invasive surgical device and then triggered to solidify or gel in the presence of ultraviolet light, visible light, or ionic change in vivo. As an example of this approach the article cites an article of Hill-West, et al., Obstet. Gynecol. 83(1):59–64 (1994).

The Hill-West et al. article, in turn, describes the use of a conformable, resorbable hydrogel barrier for preventing postoperative adhesions in animals. The article describes the formation of the hydrogel barrier in situ by photopolymerizing a solution of a macromolecular prepolymer using UV light. The hydrogel barrier is not described as being useful in weight-bearing, orthopedic applications, and in fact, was completely resorbed within 7 days after application.

There are a number of drawbacks associated with the biomaterials and related methods presently employed for orthopedic applications, and in particular joint repair and replacement. One such drawback is that these methods generally involve invasive surgery, i.e., resecting tissue in order to gain access to the injury site. In turn, invasive surgery typically involves up to 7 to 10 days of hospitalization, with the costs associated therewith.

A related drawback of an arthrotomy involves the need to cut through skin, nerves, vessels, muscles, ligaments, tendons, and/or joint capsules. Certain procedures can also require the use of either general or spinal anesthesia. They may also require blood transfusions and significant recovery time accompanied by post-surgical pain and discomfort. Lastly, prolonged physical therapy is typically required to strengthen operative areas and prevent contractures. Such therapy can often last up to six weeks or more.

It would be particularly useful to be able to repair such injuries in a manner that avoided such invasive surgical procedures and the problems associated therewith.

A number of approaches, and in turn compositions, are currently employed for such purposes as preparing prosthetic implants and repairing damaged joints and joint cartilage. Such approaches include the widespread use of artificial prosthetic implants that can be formed of an array of materials such as metals, ceramics, and bioerodible or resorbable materials. Indeed, the manufacture and use of such implants has grown exponentially in recent decades. See, for instance, "New Challenges in Biomaterials", Science, 263:1715–1720 (1994), Peppas et al.

Similarly, a number of references, and particularly those in the dental area, have described methods or apparatuses for the delivery and cure of materials within the oral cavity. Outside of the dental area, however, the number of such applications is far more limited, and includes such references as Perkins et al. (U.S. Pat. No. 4,446,578) and Oechsle III (U.S. Pat. No. 4,570,270 polyurethanes as luting agents for filling cavities in bones). See also, Kuslich (U.S. Pat. No. 5,571,189 expandable fabric spine implant device in combination with a 'graft medium' to promote fibrous union of joints); Parsons et al. (U.S. Pat. No. 5,545,229 intervertebral disc spacer formed of an elastomeric material in nucleus and annulus); Porter et al. (U.S. Pat. No. 5,591,199 curable fiber composite stent, fibrous material treated with curable material to form curable fiber composite); Glastra (U.S. Pat. No. 5,529,653 expandable double walled sleeve, space filled with curable material; and Cowan (U.S. Pat. No. 5,334,201 vascular reinforcing stent having tubular sleeve of a crosslinkable substance, the sleeve being encapsulated within a biocompatible film).

Even more recently, Applicant's U.S. Pat. No. 5,556,429 describes a joint resurfacing system which, in a preferred embodiment, involves the use of minimally invasive means to access and prepare a joint site, such as a knee, and to deliver a curable biomaterial to the prepared site and cure the biomaterial in apposition to the prepared site. The system includes the use of curable biomaterials such as silicone polymers and polyurethane polymers.

Polyurethanes themselves have been developed and used since at least the 1940's for the preparation of a variety of materials, including cast polyurethane rubbers and millable gums. Cast polyurethane rubbers can be subdivided into four general groups, including 1) unstable prepolymer systems, 2) stable prepolymer systems, 3) quasi-prepolymer systems, and 4) "one-shot" systems. See, for instance, "Polyurethanes and Polyisocanurates", Chapter 27 in Plastics Materials, J. Brydson, ed., 6$^{th}$ ed. Butterworth Heeinemann (1995).

Generally, such compositions involve the reaction of a polyhydroxy material (polyol) with an isocyanate to provide a polyurethane material. A limited number of references describe the use of components such as hydroxyl-terminated butadiene in the context of a polyurethane. Khalil, et al. (U.S. Pat. No. 5,288,797), for instance, describe moisture curable polyurethane adhesive compositions in the form of a blend of polyurethane prepolymers, together with additives (such as carbon black) and a resin, which are used to improve mechanical properties such as sag resistance. The list of polyols described as being useful for forming the prepolymer is said to include polybutadiene having at least two terminal primary and/or secondary hydroxyl groups.

Similarly, Graham et al. (U.S. Pat. No. 4,098,626) describes a hydroxy terminated polybutadiene based polyurethane bound propellant grains, while Chapin et al. (U.S. Pat. No. 4,594,380) describe an elastomeric controlled release article having a matrix formed of a polyurethane that itself is the reaction product of an isocyanate and a polyol selected from a group that includes hydroxyl-terminated polybutadiene.

While materials such as those described above are useful for their intended purposes, and have created new opportunities in their respective fields, it would be desirable to further improve various properties associated with such materials. With regard to their use as in vivo curable biomaterials, for instance, certain polyurethane compositions have been found to produce undesirable bubbles when delivered and cured in the presence of moisture. Improvement of this and other properties would be highly desirable, provided such improvement can be accomplished without undue effect on other desired and necessary properties. It would be highly desirable to have a polyurethane composition that improves the moisture cure characteristics and other properties of such a material, without detrimental effect on other necessary and preferred properties.

The development of implantable medical devices has grown dramatically over past decades. Correspondingly, those developing new and useful biomaterials for use in fabricating such devices have attempted to keep pace. The implantable medical devices can themselves take a wide variety of forms and purposes.

Many prostheses are used to replace or repair orthopedic joints. The joints of the body can be classified as between those that provide immovable articulations (synarthroidal), mixed articulations (amphiarthroidal), and movable articulations (diarthroidal). The ability of amphiarthroidal and diarthroidal joints to provide effective and pain-free articulation, and/or to serve their weight-bearing function, is generally dependent on the presence of intact, healthy cartilage within the joint.

Conventional joint prostheses are generally fabricated by the manufacturer, often as component parts of varying sizes, and selected and implanted by the surgeon in the course of invasive surgery. The applicant of the present invention, however, has demonstrated the manner in which curable biomaterials can be used to repair or resurface a joint. See, for instance, U.S. Pat. No. 5,556,429. This patent describes, for instance, the use of minimally invasive means to deliver and cure a biomaterial at a prepared site such as the knee, as well as the optional use of holes drilled into the bone, e.g., subchondral bone, that can be filled with the biomaterial to provide anchor points once cured.

The delivery of such biomaterials can take the shape of the prepared site, or can further incorporate the use of a mold, e.g., in the manner described in Applicant's corresponding PCT Patent Application No. PCT/US97/00457. In one such embodiment, for instance, a mold is provided in the form of a balloon that can be delivered to the site of an intervertebral disc space, and there filled with biomaterial in order to serve as a replacement disc.

Other examples of implanted or implantable devices include Kuslich (U.S. Pat. No. 5,571,189); Kuslich (U.S. Pat. No. 5,549,679); Parsons et al. (U.S. Pat. No. 5,545,229); Oka (U.S. Pat. No. 5,458,643); Baumgartner (U.S. Pat. No. 5,171,280); Frey et al. (U.S. Pat. No. 4,932,969); Ray et al. (U.S. Pat. No. 4,904,260); Monson (U.S. Pat. No. 4,863,477); and Froning (U.S. Pat. No. 3,875,595).

Implantable medical prostheses can take other forms as well, including other traditional types that are fabricated and packaged prior to use, and implanted in either a transitory, temporary or permanent fashion within the body. Such prostheses can be used, for instance, as or in connection with passageways within the body such as catheters, such as stents and shunts. Other examples of devices implantable on at least a transitory basis include catheters such as balloon catheters. See, for example, the following U.S. Patents to Walinsky (U.S. Pat. No. 5,470,314); Saab (U.S. Pat. No. 5,411,477); Shonk (U.S. Pat. No. 5,342,305); Trotta et al. (U.S. Pat. No. 5,290,306); Tower (U.S. Pat. No. 4,913,701); Oechsle III (U.S. Pat. No. 4,570,270); and Perkins et al. (U.S. Pat. No. 4,446,578).

The use of stents, in particular, has become accepted as a means for preventing abrupt vessel closure and restenosis following balloon angioplasty and over the past decade has grown dramatically as problems inherent in early designs have been overcome. Typically, stents are constructed from nonthrombogenic materials of sufficient flexibility (in their unexpanded state) to allow passage through guiding catheters and tortuous vessels. Such stents are typically radiopaque to allow fluoroscopic visualization. To date, most coronary stents have been constructed from either stainless steel or titanium, e.g., in the form of an expandable mesh, wire coil, slotted tube, or zigzag design.

Recent developments have included the use of balloon-expandable stents. Such stents are available in a number of configurations, such as the Gianturco-Roubin Flex-Stent (Cook, Inc.), the Palmax-Schatz Coronary Stent (Johnson & Johnson), Wiktor Stent (Medtronic, Inc.), Strecker Stent (Boston Scientific), ACS Multi Link Stent (Advanced Cardiovascular Systems, Inc.) the AVE Micro Stent (Applied Vascular Engineering) and Cordis Stent (Cordis Corp.). Even more recently, temporary stents (e.g., removable or biodegradable) have been developed, in an effort to achieve the structural support and lumen stabilizing benefits of permanent stenting without the problem of thrombosis.

Most stents, and certainly most, if not all, commercially available stents, are manufactured and sterilized by the manufacturer, and provided in an insertable form. Other approaches have been described, however, including modification of the stent material either pre or post-delivery. See, e.g., Porter et al., U.S. Pat. No. 5,591,199 (for a "Curable Fiber Composite Stent and Delivery System"). In spite of recent accomplishments, many stents available today continue to encounter problems upon insertion (e.g., lack of flexibility) and/or over the course of their use (e.g., erosion, tissue incompatability).

In a similar manner, a variety of preformed catheters and shunts have been developed in the form of tubular instruments to allow passage of fluid from, into, or between body cavities. Relatively few of the many known catheters are formed or prepared in situ. Recent patents of Glastra (U.S. Pat. Nos. 5,344,444 and 5,529,653) describe, for instance, a method for the fabrication and use of an expandable hollow sleeve for local support or reinforcement of a body vessel. The hollow sleeve is described as having a curable material, such as an "acrylate", contained within an absorbent material within the sleeve. In a different approach, Cowan (U.S. Pat. No. 5,334,201) describes a stent made of a crosslinkable material, by a method that involves encapsulating an uncured stent in a biologically compatible film, transluminally inserting the stent/film into position, and curing the stent.

Preformed catheters and grafts have also been used in the treatment of abdominal aortic aneurysms. The ultimate goal in the treatment of aortic aneurysms is to exclude the aneurysm from the aortic bloodstream without interfering with limb and organ perfusion. Direct surgical repair of such aneurysms is associated with high morbidity and mortality. The technique of placing a prosthetic graft into the opened aneurysm and suturing it to "normal" aorta above and below requires extensive intraabdominal or retroperitoneal dissection, as well as interruption of blood flow during completion of the anastomoses, under general anesthesia.

Methods and materials used to prepare implantable prostheses, as described above, can be contrasted to those used in the burgeoning dental field, in which polymers play an important role as ingredients of composite restorative materials, cements and adhesives, cavity liners and protective sealants. See, for instance, Brauer and Antonucci, "Dental Applications" pp 257–258 in Concise Encyclopedia of Polymer Science and Engineering.

At times, the preparation of such dental prostheses relies on the use of molds taken of parts of the body in order to then cast or otherwise form prosthetic replacement parts. See, for instance, Weissman, U.S. Pat. No. 4,368,040 for "Dental impression tray for forming a dental prosthesis in situ". See also, "Process for making a prosthetic implant", Kaye U.S. Pat. No. 5,156,777, which involves the use of three-dimensional data to prepare a life size model of an organ site, which in turn is used to cast a prosthetic implant.

Clearly the ability to mold body parts, such as teeth, in order to form prosthetic devices is considerably different than the preparation and delivery of preformed implants themselves, particularly for implants used in internal sites or tissues that are not as readily accessible as the oral cavity. Among the several distinctions between preformed implantable prostheses and those formed in situ are the fact that the latter are typically restricted to external or surgically accessible sites or tissues. In these situations, the ability to deliver a material used to form a prosthesis at an accessible site, although certainly demanding in many respects, has far fewer considerations than a material intended for delivery and use internally.

A number of problems that continue to affect the further development of some or all of the above-described implanted prostheses, include problems that affect the preparation of the prostheses themselves, their delivery to the site of use, and their interactions with the host or surrounding tissue in the course of their use.

For example, the physician cannot correct the size and shape of the prostheses once it has been introduced to the body; therefore, all measurements and adjustments of size must be made preoperatively. In the case of aortic grafts, the aorta may continue to enlarge and thus pull away from the fixation stent. Problems associated with the healing interface between the stent, the graft, and the aorta is not known, and the graft may dislodge and migrate, causing acute iliac occlusion. The aneurysm may continue to function despite an intact functioning endovascular graft.

It would clearly be desirable to have a system that permits prostheses to be prepared and used in a manner that overcomes some or all of these concerns.

SUMMARY OF THE INVENTION

The present invention overcomes the drawbacks associated with the prior art by providing a method, and related composition and apparatus for repairing or resurfacing the site of injured tissue by minimally-invasive means.

In one embodiment, the method of the present invention comprises the steps of:

(a) providing a curable biomaterial; and (b) employing minimally invasive means to:
  (i) prepare the tissue injury site for receipt of the biomaterial;
  (ii) deliver a quantity of the curable biomaterial to the prepared tissue injury site;
  (iii) cure the delivered biomaterial in such a manner that the cured biomaterial is permanently retained in apposition to the prepared site; and
  (iv) contour the cured, retained biomaterial to achieve a desired conformation approximating that of natural tissue.

The method of the invention lends itself to a corresponding system that comprises curable biomaterial, in combination with minimally invasive means for preparing the tissue site; delivering the biomaterial to the prepared tissue site; curing the biomaterial in situ; and contouring the cured biomaterial. The individual components of such a system, and particularly means for delivering and curing biomaterial in a minimally invasive fashion are considered novel as well.

In a preferred embodiment, a system is provided that comprises: (a) an arthroscopic surgical instrument; and (b) a fluid delivery cannula capable of delivering a flowable, curable biomaterial under arthroscopic visualization, the biomaterial comprising a curable polymer and hydrogel.

The preferred system can be used to perform a method that comprises the steps of:

(a) providing a flowable, curable biomaterial comprising a curable biomaterial;

(b) preparing the tissue injury site by operation of the arthroscopic instrument, and under arthroscopic visualization;

(c) preparing a tissue access site to include anchor points in the subchondral bone and inserting and directing the delivery cannula through the tissue access site to the site of tissue injury;

(d) delivering a quantity of the curable biomaterial through the cannula to the prepared site;

(e) curing the delivered biomaterial by minimally invasive means and in a manner such that the cured biomaterial is retained in apposition to the prepared site; and (f) contouring the cured biomaterial to achieve a desired conformation approximating that of natural tissue.

In an alternative embodiment, the cured, shaped biomaterial can be treated or modified in order to improve one or more desirable properties, for instance, it can be coated with a permanent interface material in order to improve the biocompatibility or coefficient of friction of the final implant.

In another aspect, the present invention provides a curable polyurethane composition comprising a plurality of parts capable of being sterilized, stably stored, and mixed at the time of use in order to provide a flowable composition and initiate cure, the parts including: (1) a quasi-prepolymer component comprising the reaction product of one or more polyether polyols, one or more isocyanates, and one or more reactive hydrophobic additives, and (2) a curative component comprising one or more polyether polyols, one or more chain extenders, one or more catalysts, and optionally, other ingredients such as an antioxidant and dye. Upon mixing, the composition is sufficiently flowable to permit it to be delivered to the body by minimally invasive means, and there fully cured under physiologically acceptable conditions. Preferably, the component parts are themselves flowable, or can be rendered flowable, in order to facilitate their mixing and use.

Applicants have discovered, inter alia, that the presence of the reactive hydrophobic additive of the prepolymer provides several unexpected and desirable features, both in the formulation and use of the prepolymer itself, as well as in the mixed composition. These features include an improved combination of such properties as moisture cure characteristics, cross-linking, viscosity, compression fatigue, and stability. In particular, the use of the polymer significantly lessens, and can avoid altogether, the appearance of bubbles seen previously with polyurethane compositions cured in vivo in the presence of moisture. While not intending to be bound by theory, it appears that the presence of a sufficient amount of hydrophobic or nonpolar additive, and particularly one that is miscible with the polyether component, alters or affects the surface tension (e.g., as determined by the contact angle) of the resulting composition, and in turn, permits the composition to cure with a significant reduction in the appearance of bubbles. Surprisingly, this and other improved characteristics are not achieved at the sacrifice of other desirable properties.

In a preferred embodiment, within the prepolymer, the polyether component is present at a concentration of between about 2% and about 10%, and preferably between about 4% and about 8% by weight, based on the weight of the composition, and is selected from the group consisting of linear or branched polyols with polyether backbones of polyoxyethylene, polyoxypropylene, and polytetramethylene oxide (polyoxytetramethylene), and copolymers thereof. A particularly preferred polyol is polytetramethylene oxide, preferably of relatively low molecular weights in the range of 250 to 2900, and combinations thereof.

In a further preferred embodiment the isocyanate is present in excess in the prepolymer component, e.g., at a concentration of between about 30% and about 50%, and preferably between about 35% and about 45%, by weight. The isocyanate is preferably an aromatic (poly)isocyanate selected from the group consisting of 2,2'-, 2,4'-, and 4,4'-diphenylmethanediisocyanate (MDI), and combinations thereof.

In such an embodiment, the reactive polymer additive itself is present at a concentration of between about 1% and about 50% by weight, and is selected from the group consisting of hydroxyl- or amine-terminated compounds selected from the group consisting of poybutadiene, polyisoprene, polyisobutylene, silicones, polyethylenepropylenediene, copolymers of butadiene with acryolnitrile, copolymers of butadiene with styrene, copolymers of isoprene with acrylonitrile, copolymers of isoprene with styrene, and mixtures of the above. In a particularly preferred embodiment the additive comprises hydroxyl-terminated polybutadiene, present at a concentration of between about 5% and about 30%, by weight, and preferably between about 5% and about 20% by weight.

In a further preferred embodiment, the polyether polyol of the curative component is as described above with regard to the prepolymer and is present at a final concentration of between about 20% and 60%, and preferably between about 30% and about 45%, by weight. In such an embodiment, the chain extender comprises a combination of linear (e.g., cyclohexane dimethanol ("CHDM")) and branched (e.g, trimethyloyl propane ("TMP") chain extenders, with the former being present at a final concentration of between about 1% and 20% (and preferably between about 5% and about 15%), and the latter being present at a final concentration of between about 1% and about 20%, and preferably between about 1% and about 10%, by weight of the final composition.

Surprisingly, the composition provides improved properties, including an improved combination of such properties as hardness, strength and/or cure characteristics (particularly in the presence of moisture), as compared to compositions previously known. More surprisingly, Applicants have discovered that such improvement can be achieved without detrimental effect on other desired properties, including those that arise (a) prior to delivery, (b) in the course of delivery (including whatever mixing, curing, and/or shaping that may occur), and finally, (c) following cure and in the course of extended use in the body.

In another aspect, the invention provides a cured composition, prepared as the reaction product of a plurality of parts as described herein. In yet another aspect, the invention provides a kit that can be used to prepare a composition and/or that itself includes a composition as a component part. A kit, for instance, may take the form of a composition (or its components) in combination with pre-formed device components or accessories, such as an implantable mold apparatus for shaping and restraining the composition. Optionally, a kit can also include a composition (or its components or parts) in combination with a delivery device adapted to deliver the composition to the site of tissue injury. Optionally, a kit may also take the form of a composition, either as its component parts and/or in combination with other ingredients or materials, such as a filler or hydrogel (used to form a matrix), or together with an implantable prosthetic device. In any such kit, it is envisioned that a kit may include one or more protocols or instructions for use.

In yet another aspect, the invention provides a method of preparing and a method of using such a composition. In a further aspect, the invention provides a cured composition (optionally within a mold apparatus), for use in apposition to a joint surface, as well as the combination of such a joint surface with a cured composition (optionally within a mold apparatus) in apposition thereto.

In yet another aspect, the present invention provides an apparatus and method for forming a prosthesis, in situ, the method, in a preferred embodiment, comprising the steps of:

a) providing an implantable mold apparatus comprising a cavity adapted to receive and contain a flowable biomaterial and a conduit adapted to connect the cavity to a source of curable, flowable biomaterial, b) inserting the mold, preferably by minimally invasive means, to a desired site within the body, c) delivering biomaterial to the mold in order to fill the cavity to a desired extent, d) permitting the biomaterial to cure to a desired extent, and e) employing the molded biomaterial in situ as a prosthetic device.

The apparatus, in turn, provides an implantable mold apparatus comprising an expandable cavity adapted to receive and contain a flowable biomaterial in a geometry, configuration and/or position optimal for the intended purpose, and a conduit adapted to connect the cavity to a source of curable, flowable biomaterial. The conduit is preferably removable from the filled cavity, e.g., by cutting it at or near the point where it joins the cavity. Optionally, and preferably, the apparatus further includes means for providing positive or negative air pressure within or to the biomaterial cavity, in order to facilitate the delivery of biomaterial and/or to affect the final shape of the cured mold.

The apparatus and method can be used for a variety of applications, including for instance, to provide a balloon-like mold for use preparing a solid or intact prosthesis, e.g., for use in articulating joint repair or replacement and intervertebral disc repair. Alternatively, the method can be used to provide a hollow mold, such as a sleeve-like tubular mold for use in preparing implanted passageways, e.g., in the form of catheters, such as stents, shunts, or grafts.

In yet another aspect, the invention provides a mold apparatus useful for performing a method of the invention, e.g., in the form of an inflatable balloon or tubular mold, preferably in combination with the conduit used to deliver biomaterial. Along these lines, the invention further provides a system useful at the time of surgery to prepare an implanted prosthesis in vivo, the system comprising a mold apparatus (e.g., cavity and conduit) in combination with a supply of curable biomaterial, and optionally, with a source of positive and/or negative air pressure.

In a further aspect, the invention provides a corresponding prosthesis formed by a method of the present invention, including for instance, an implanted knee prosthesis, intervertebral disc prosthesis, and a tubular prosthesis for use as a catheter, such as a stent, shunt, or graft (e.g., vascular graft). The present invention further provides surgical kits that include a mold apparatus as presently described, in combination with a corresponding drilling template, and a kit in which a mold apparatus is provided in combination with a supply (e.g., sufficient for a single use) of biomaterial itself.

BRIEF DESCRIPTION OF THE DRAWING

In the Drawing:

FIG. 8 shows a preferred embodiment of a mold apparatus, in uninflated and unfilled form, in the form of a tubular system for preparing an implanted passageway in situ.

FIG. 9 shows the mold of FIG. 8 in a form wherein relevant portions have been filled with air and biomaterial.

FIG. 10 shows a cross section of the mold apparatus of FIG. 9, taken along lines 10—10.

DETAILED DESCRIPTION

Figure 1:
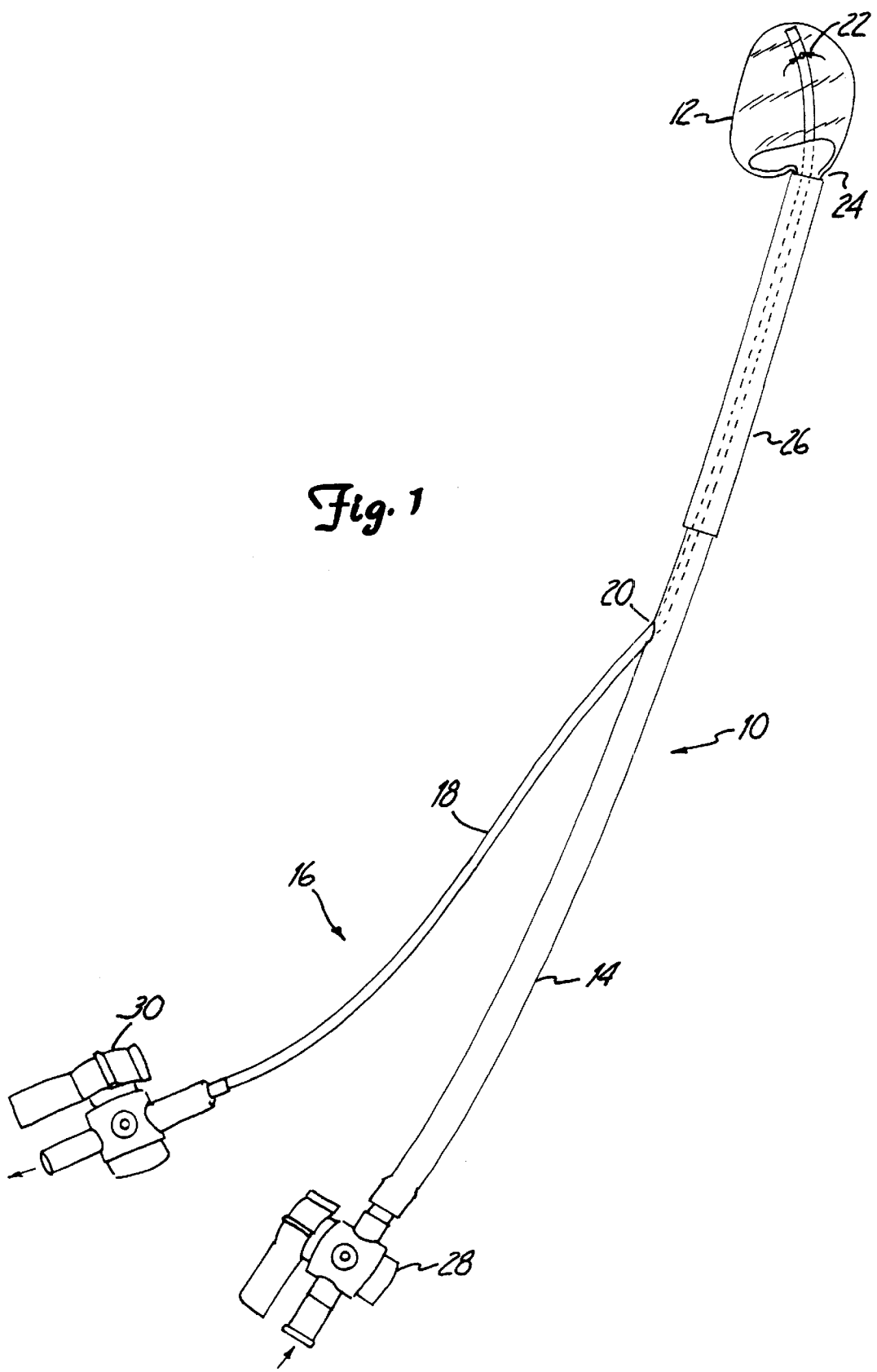
FIG. 1 shows a top plan view of a mold apparatus including a balloon cavity and biomaterial delivery conduit for use in intervertebral disc replacement.

The present invention provides a method and system for the repair of natural tissue that involve the delivery of a biomaterial composition using minimally invasive means, the composition being curable in situ in order to provide a permanent replacement for natural tissue. Optionally, and preferably, the biomaterial is delivered to a mold apparatus that is positioned by minimally invasive means and filled with biomaterial composition, which is then cured in order to retain the mold and cured composition in situ.

As used herein the following words and terms shall have the meanings ascribed below:

"repair" will refer to the use of a composition to augment, replace or provide some or all of the structure or function of natural tissue in vivo, for instance, to provide an implant such as a catheter, or to repair (e.g., reconstruct or replace) cartilage, such as fibrocartilage or hyaline cartilage present in a diarthroidal or amphiarthroidal joint. Repair can take any suitable form, e.g., from patching the tissue to replacing it in its entirety, preferably in a manner that reconstructs its natural or other desired dimensions;

"cure" and inflections thereof, will refer to any chemical, physical, and/or mechanical transformation that allows a composition to progress from a form (e.g., flowable form) that allows it to be delivered to the joint site, into a more permanent (e.g., cured) form for final use in vivo. When used with regard to the method of the invention, for instance, "curable" can refer to uncured composition, having the potential to be cured in vivo (as by catalysis or the application of a suitable energy source), as well as to a composition in the process of curing (e.g., a composition formed at the time of delivery by the concurrent mixing of a plurality of composition components). As further described herein, the cure of a composition can generally be considered to include three stages, including (a) the onset of gelation, (b) a period in which gelation occurs and the composition becomes sufficiently tack-free to permit shaping, and (c) complete cure to the point where the composition has been finally shaped for its intended use.

"minimally invasive means" refers to surgical means, such as microsurgical or endoscopic or arthroscopic surgical means, that can be accomplished with minimal disruption of the pertinent musculature, for instance, without the need for open access to the tissue injury site or through minimal incisions (e.g., incisions of less than about 4 cm and preferably less than about 2 cm). Such surgical means are typically accomplished by the use of visualization such as fiberoptic or microscopic visualization, and provide a post-operative recovery time that is substantially less than the recovery time that accompanies the corresponding open surgical approach;

"endoscopic/arthroscopic surgical instrument" refers to the controllers and associated hardware and software necessary for performing conventional endoscopic or arthroscopic surgery; and "delivery cannula" shall mean a cannula or other delivery device capable of being operated in a minimally invasive fashion, e.g., under arthroscopic visualization, and optionally together with associated connective tubing and containers for the operable and fluid attachment of the cannula to a source of composition for the storage, delivery, and recovery of compositions of the present invention.

"mold" will refer to the portion or portions of an apparatus of the invention used to receive, constrain, shape and/or retain a flowable biomaterial in the course of delivering and curing the biomaterial in situ. A mold may include or rely upon natural tissues (such as the annular shell of an intervertebral disc) for at least a portion of its structure, conformation or function. The mold, in turn, is responsible, at least in part, for determining the position and final dimensions of the cured prosthetic implant. As such, its dimensions and other physical characteristics can be predetermined to provide an optimal combination of such properties as the ability to be delivered to a site using minimally invasive means, filled with biomaterial, and optionally, then remain in place as or at the interface between cured biomaterial and natural tissue. In a particularly preferred embodiment the mold material can itself become integral to the body of the cured biomaterial.

As described herein, a mold apparatus will generally include both a cavity for the receipt of biomaterial and a conduit for the delivery of biomaterial to that cavity. Some or all of the material used to form the cavity will generally be retained in situ, in combination with the cured biomaterial, while some or all of the conduit will generally be removed upon completion of the method. An implanted prosthesis, in turn, can be used to replace, provide, or supplement the structure or function of natural tissue in vivo. The prosthesis can take any suitable form, e.g., including patching, repairing or replacing tissue (such as knee or intervertebral disc), supporting existing tissue (as by a stent, for instance), or creating new material having a tissue like function (as by a shunt).

The word "biomaterial" will be used interchangeably with the word "composition", when used in the context of the present invention, and will generally refer to a material that is capable of being introduced to the site of a joint and cured to provide desired physical-chemical properties in vivo. In a preferred embodiment the term will refer to a material that is capable of being introduced to an site within the body using minimally invasive means, and cured or otherwise modified in order to cause it to be retained in a desired position and configuration. Generally such biomaterials are flowable in their uncured form, meaning they are of sufficient viscosity to allow their delivery through a cannula of on the order of about 1 mm to about 6 mm inner diameter, and preferably of about 2 mm to about 3 mm inner diameter. Such biomaterials are also curable, meaning that they can be cured or otherwise modified, in situ, at the tissue site, in order to undergo a phase or chemical change sufficient to retain a desired position and configuration.

Method and System

In a preferred embodiment, the present invention provides a method and related materials and apparatus for repairing diarthroidal and amphiarthroidal joints by minimally invasive means. The method involves the use of minimally invasive means to prepare the site of injury, deliver a curable biomaterial to the joint site, and to cure the biomaterial in situ in order to repair hyaline cartilage and/or fibrocartilage.

According to a preferred embodiment, a liquid phase polymeric composite material (e.g., formed of a two-part polyurethane system) is applied through a cannula under arthroscopic visualization. The composite is cured and contoured in situ to effectively resurface a damaged joint. The cured polymer composite exhibits physical/chemical characteristics analogous to those of human cartilage, and demonstrates an optimal combination of such properties as load bearing, shear stress resistance, impact absorption, and wear characteristics. The surface of the cured composite can optionally be modified after curing and contouring, e.g., in order to reduce its coefficient of friction.

In a preferred embodiment, the method of the present invention comprises the step of providing a curable biomaterial comprising a curable polymer, optionally in combination with a hydrogel. Biomaterials suitable for use in the present invention include those materials that are capable of being delivered by means of a cannula, as described herein, and cured in situ in order to form a replacement material for bone or cartilage.

Natural cartilage is a non-vascular structure found in various parts of the body, and particularly articular cartilage, which exists as a glycosamine matrix with a fibrillar scaffold of Type II collagen. Chondrocytes are typically interspersed in the matrix. Its natural elasticity enables it to break the force of concussions, while its smoothness affords ease and freedom of movement. In terms of thickness, cartilage tends to take on the shape of the articular surface on which it lies. Where this is convex, the cartilage is thickest at the center, where the greatest pressure is received. The reverse is generally true in the case of concave articular surfaces.

Preferred biomaterials are intended to mimic many of the physical-chemical characteristics of natural cartilage. Preferred biomaterials are composites of two or more individual materials, and particularly those comprising two phase systems formed from a polymeric matrix and a hydrogel filler. Particularly preferred biomaterials are polyurethane systems of the type described herein.

The method of the invention can be used to repair a number of tissues, including a variety of joints, and is particularly useful for diarthroidal and amphiarthroidal joints. Examples of suitable amphiarthroidal joints include the synphysoidal joints, such as the joints between bodies of the vertebrae. Such joints provide surfaces connected by fibrocartilage, and have limited motion. Other examples include syndesmoidal joints, having surfaces united by an interosseous ligament, as in the inferior tibio-fibular joint.

Examples of suitable diarthroidal joints include the ginglymus (a hinge joint, as in the interphalangeal joints and the joint between the humerus and the ulna); throchoides (a pivot joint, as in superior radio-ulnar articulation and atlanto-axial joint); condyloid (ovoid head with elliptical cavity, as in the wrist joint); reciprocal reception (saddle joint formed of convex and concave surfaces, as in the carpo-metacarpal joint of the thumb); enarthrosis (ball and socket joint, as in the hip and shoulder joints) and arthrodia (gliding joint, as in the carpal and tarsal articulations).

In a particularly preferred embodiment, the method and system of the present invention are used to resurface a joint selected from the group consisting of enarthroidial ("ball and socket") joints, and in particular the hip and shoulder joints, and ginglymo-arthroidal ("hinge") joints, and in particular the temporo-mandibular joint. Such joints provide a particularly unique advantage in that one or more components of the natural joint can themselves be temporarily repositioned in order to contour the biomaterial as it cures.

A degenerative shoulder joint is repaired, for instance, by resurfacing either the humeral head, or preferably, the glenoid fossa. The glenoid fossa is arthroscopically exposed and the residual cartilage is removed by burrs and cutters. Optionally, and preferably, the humeral head is smoothed and all roughened cartilage surfaces removed. With the patient suitably positioned, a curable biomaterial is delivered allowed to flow smoothly into the glenoid fossa. With the polymer in a non-tacky, but moldable stage of cure the humeral head is repositioned into the glenoid for use in molding the polymer as it continues to cure. In an alternative to the use of minimally invasive means, the process can be performed using invasive surgical procedures, given the unique qualities of the biomaterial.

A degenerative hip joint is repaired in a similar manner, for instance, by resurfacing either the femoral head, or preferably, the acetabular cup. The cup is arthroscopically exposed and the residual cartilage is removed by burrs and cutters. Optionally, and preferably, the femoral head is smoothed and all roughened cartilage surfaces removed. With the patient suitably positioned, a curable biomaterial is delivered allowed to flow smoothly into the acetabular cup. With the polymer in a non-tacky, but moldable stage of cure the femoral head is repositioned into the acetabulum for use in molding the polymer as it continues to cure. In an alternative to the use of minimally invasive means, the process can be performed using invasive surgical procedures, given the unique qualities of the biomaterial.

A degenerative temporo-mandibular joint can be arthroscopically repaired using two small portals. Through one portal a needle arthroscope is placed for visualization of the temporomandibular joint. Through the second portal the surface of the maxillar portion is prepared and the mandible ramus surface is smoothed. Optionally, anchor points are cut in the maxilla. With the patient suitably positioned, a curable biomaterial is delivered and allowed to flow smoothly into the covered socket. With the polymer in a non-tacky, but moldable stage of cure the ramus of the mandible is repositioned and compressed into the socket for use in molding the polymer as it continues to cure. As an alternative to the use of minimally invasive means, each of these processes can be performed using invasive surgical procedures, given the unique qualities of the biomaterial.

Biomaterial Compositions

Applicants have discovered that one or all of the improved properties set forth above can be achieved without detrimental effect on other properties of the composition, either before, during or following delivery and cure. The term "detrimental effect", as used herein, refers to an effect on one or more other properties that would render the composition unsuitable for its intended use.

The musculoskeletal system, and more often its articulating joints, are subject to injury caused by traumatic events or diseases such as osteoarthritis and rheumatoid arthritis. Inherent lubricity of joint's connective tissue, the cartilage, is affected. The non-functioning cartilage causes, in turn, abnormal wear and tear of both the connective tissue and bones. This process often results in progressive, crippling pain. With in vivo tissue repair via cell transplant and implantation in its infancy and total joint athroplasty not always a practical solution, the need for alternative treatment is quite obvious.

We have developed methodology which utilizes minimally invasive athroscopic surgery to remove damaged cartilage followed with application of liquid, in situ cured polymer to resurface the tibial plateau of the knee joint. Two component PTMO polyether-based polyurethane system has been chosen as the polymer of choice. The MDI quasi prepolymer approach was selected to liquefy the MDI isocyanate and controlled cross-linking in the hard segment was utilized to achieve needed biodurability. In order to manage "isothermal curing environment" of in vivo application, delayed action catalysis with Tin/amine synergism was used. The system was mixed and delivered to the athroscopically prepared site via delivery device with static mixer/cannula combination, then shaped and cured to its desired shape.

Physical-mechanical properties were determined according to ASTM Methods and in vitro biodurability via accelerated oxidative/hydrolytic degradation. In vivo function in the knee of ovine (sheep) model were determined at 3, 12, 26 and 52 weeks of implantation.

Physical-mechanical properties of the polyurethane system can be highlighted by Hardness of 70–75A Shore, Tensile Strength of 60–75 Mpa, Ultimate Elongation of 350–450% and Die "C" Tear of 28–44 kN/M. Compression Moduli were determined at 4.48 kN load and indicated deformation of 20–40%. Finally, compression fatigue, at 2.2 kN force indicated that $1.5 \times 10^7$ cycles, at 10 cycles/sec, did not alter compression moduli of the polymer.

The system does not generate cytotoxic by-products when cured in n-saline, at 23° C., between 10 seconds and 24 days testing period. Finally, necropsy at time of sacrifice of the animal models revealed essential integrity of the implant and no adverse tissue reaction was detected by histopathology. Encouragingly, signs of cartilage regeneration were detected at tissue/polyurethane interface. We can conclude that in situ cured polyurethanes, combined with minimally invasive athroscopic procedure represent novel, promising way to resurface damaged body joints.

Concepts governing in vivo resurfacing of damaged articular cartilage by in situ curable polymers are outlined above. Briefly reviewed, a pre-polymer is delivered to the "repair site" by athroscopic procedure, shaped and polymerized in situ to restore and augment cushioning and lubricating functions of the cartilage. Material selection, its mechanical properties, biodurability and in vivo performance are subject of this paper.

The polymer system one must have certain key characteristics: (1) it should be amenable to microphase separation and domain formation to mimic the cartilage; (2) the system must be liquid at delivery; (3) polymerization kinetics must be fast and fully controllable; (4) no toxic or otherwise harmful by-products can be released; (5) resultant polymer must have broad range of mechanical properties, excellent loan bearing, fatigue and wear resistance; (6) the system should be amenable to form microcellular structure; (7) lastly, the polymer must biodurable. Polyurethanes could be the chosen one.

Although aromatic polyurethanes based on polycarbonate polyols are considered most resistant to stress- and oxidation-driven Environmental Stress Cracking, we have selected PTMO-based polyols recognized for their superb hydrolytic resistance. A two component system with MDI-quasi-prepolymer component "A" and OH-terminated intermediates as component "B" was used. Blend of polyols was the choice to keep their melting temperature close to the ambient. The "delayed action" fast curing kinetics was achieved with Tin compound/tertiary amine based catalyst system. Gel times of 10–40 sec. with predominant cure of 2–5 min. are required to mix, deliver, cure and shape the polyurethane. Such short times are preferred to lower total curing exotherm but require chemical cross-linking to augment virtual ones formed by hard segment domains. This is accomplished, in such soft materials with target harness of 60–80 Shore A, by the blend of linear and polyfunctional chain extenders. This also generates unique tensile and compression behavior similar to those of x-linked rubber and highlighted by Tensile strength of 60–75 Mpa, elongation of more than 300% and Compression fatigue in excess of 20 million cycles at 2.2 kN force. Finally, two-plus years of in vivo biodurability is expected as determined by hydrogen peroxide/cobalt chloride testing.

To enhance cushioning function and to promote tissue integration, microcellular structure can be achieved by controlled nucleation of $N_2$ gas. We can conclude that polyurethanes are ideally suited for in vivo resurfacing of articular cartilage.

Natural cartilage is a non-vascular structure found in various parts of the body. Articular cartilage tends to exist as a fine granular matrix forming a thin incrustation on the surfaces of joints. The natural elasticity of articular cartilage enables it to break the force of concussions, while its smoothness affords ease and freedom of movement. In one embodiment a preferred composition is intended to mimic many of the physical, chemical and/or mechanical characteristics of natural cartilage. In an another preferred embodiment, a composition of this invention provides a useful implant in the form of a catheter, e.g., a stent, graft or shunt, by the use of a mold apparatus as described above. In such an embodiment the cured composition provides a number of characteristics, including biocompatability, strength, and the like.

Compositions can be provided as one component systems, or as two or more component systems that can be mixed (or partially mixed) prior to or during delivery, or at the site of repair. Generally such compositions are flowable in their uncured form, meaning they are of sufficient viscosity to allow their delivery through a cannula of on the order of about 2 mm to about 6 mm inner diameter, and preferably of about 3 mm to about 5 mm inner diameter. Such compositions are also curable, to enable them to be polymerized or otherwise modified, in situ, during delivery and/or at the tissue site, in order to undergo a phase or chemical change sufficient to retain a desired position and configuration.

When cured, suitable materials can be homogeneous, providing the same physico-chemical properties throughout, or they can be heterogeneous and exhibit varying features or properties. An example of a suitable homogeneous composition, as presently used for knee joint repair, is described below. An example of a heterogeneous composition, e.g., for use as an intervertebral disc replacement, is a composition that mimics the natural disc by providing a more rigid outer envelope (akin to the annulus) and an more liquid interior core (akin to the nucleus). Such heterogeneous compositions can be prepared by the use of a single composition, e.g., by employing varying states of cure and/or by the use of a plurality of compositions, including varying compositions of the same ingredients used to form the composition.

Suitable compositions for use in the present invention are those polymeric materials that provide an optimal combination of properties relating to their manufacture, application, and in vivo use. In the uncured state, such properties include processability, and the ability to be safely sterilized and stored. In the course of applying such compositions, suitable materials exhibit an optimal combination of such properties as flowability, moldability, and in vivo curability. In the cured state, suitable compositions exhibit an optimal combination of such properties as cured strength (e.g., tensile and compressive), softness/stiffness ratio, biocompatability and biostability.

When cured, the compositions demonstrate an optimal combination of properties, particularly in terms of their conformational stability and retention of physical shape, dissolution stability, biocompatability, and physical performance, as well as physical properties such as density and surface roughness, and mechanical properties such as load-bearing strength, tensile strength, shear strength, shear fatigue, impact absorption, wear characteristics, and surface abrasion. Such performance can be evaluated using procedures commonly accepted for the evaluation of natural tissue and joints, as well as the evaluation of materials and polymers in general. In particular, a preferred composition, in its cured form, exhibits mechanical properties that approximate or exceed those of the natural tissue it is intended to provide or replace.

Preferred components of compositions, and compositions themselves, are also stable under conditions used for sterilization, and additionally are stable on storage and in the course of delivery. They are also capable of flowing through a delivery cannula to an in vivo location, and being cured in situ, as by chemical catalysis, by exposure to an energy source such as ultraviolet light, or by chemical reaction producing exotherm. Thereafter the cured composition is suitably amenable to shaping and contouring, by the use of conventional or custom designed arthroscopic tools or instruments. Over the course of its use in the body the cured, contoured composition exhibits physiological, physical-chemical and mechanical properties suitable for use in extended in vivo applications.

Components

A "polymer system", as used herein refers to the component or components used to prepare a polymeric composition of the present invention. In a preferred embodiment, a polymer system comprises the components necessary to form two parts: Part I being an isocyanate-functional polyurethane pre-polymer (optionally referred to as an "isocyanate quasi-polymer"). The quasi-polymer of Part I typically includes a polyol component in combination with a hydrophobic additive component and an excess of an isocyanate component. Part II of the two component system can include one long-chain polyols, chain extenders and/or cross-linkers, together with other ingredients (e.g., catalysts, stabilizers, placticizers, antioxidants, dyes and the like). Such adjuvants or ingredients can be added to or combined with any other component thereof either prior to or at the time of mixing, delivery, and/or curing.

In a particularly preferred embodiment, a polymer system of this invention is provided as a plurality of component parts and employs one or more catalysts. The component parts, including catalyst, can be mixed to initiate cure, and then delivered, set and fully cured under conditions (e.g., time and exotherm) sufficient for its desired purpose. Upon the completion of cure, the resultant composition provides an optimal combination of properties for use in repairing or replacing injured or damaged tissue. In the course of curing, a suitable composition provides a bulk exotherm (within samples sizes suitable for in vivo use) of between about 100 degrees C. and about 140 degrees C., and preferably between about 110 degrees C. and about 130 degrees C., and a surface exotherm of between about 50 degrees C. and about 80 degrees C., and preferably between about 60 degrees C. and about 70 degrees C.

In order to obtain a cured composition having desired physical-chemical, mechanical and physiological properties, a significant factor in the choice of appropriate isocyanate, polyol and chain extender/cross linker are their chemical composition and molecular weight. A composition of this invention can be expressed in terms of both: (1) the free isocyanate number ("FNCO") (also known as the isocyanate equivalent), which can be defined as the average molecular weight of the isocyanate divided by the number of isocyanate functional groups, and (2) the average hydroxyl number (also know as hydroxyl equivalent weight), which can be defined as the average molecular weight of the polyol(s) divided by the average number of reactive hydroxyl groups per mole of polyol(s).

The isocyanate component can be provided in any suitable form, examples of which include 2,4'-diphenylmethane diisocyanate, 4,4'-diphenylmethane diisocyanate, and mixtures or combinations of these isomers, optionally together with small quantities of 2,2'-diphenylmethane diisocyanate (typical of commercially available diphenylmethane diisocyanates). Other examples include aromatic polyisocyanates and their mixtures or combinations, such as are derived from phosgenation of the condensation product of aniline and formaldehyde. It is suitable to use an isocyanate that has low volatility, such as diphenylmethane diisocyanate, rather than more volatile materials such as toluene diisocyanate. An example of a particularly suitable isocyanate component is the 4,4'-diphenylmethane diisocyanate ("MDI"), preferably provided in liquid form as a combination of 2,2'-, 2,4'- and 4,4'-isomers of MDI.

For a suitable composition, the stoichiometery between Parts I (quasi prepolymer) and II (curative component), expressed in terms of the NCO:OH ratio of the isocyanate pre-polymer (Part I) and the polyol components (Part II) is preferably within the range of about 0.8 to 1 to about 1.2 to 1, and more preferably between about 0.9 to 1 to about 1.1 to 1. It has been found that NCO:OH ratios of less than about 0.8 to 1 tend to provide less than desired cure kinetics or physical-mechanical properties upon cure. Those ratios greater than about 1.1 to 1, in turn, tend to increase the potential for cytotoxicity or for adverse tissue reaction characterized by over crosslinking via internal allophanate or biuret links, generated by an excess of FNCO groups.

The polyol component can be provided in any suitable form as well. As used herein, the term "polyol" includes virtually any functional compound having active hydrogens in accordance with the well-known Zerevitinov test, as described for instance in Chemistry of Organic Compounds by Carl R. Noller, Chapter 6, pp. 121–122 (157), the disclosure of which is incorporated herein by reference. Thus, for example, amine terminated polyethers and polyolefins, thiols, polyimines, and polyamines can also be used as polyols in the present invention. In such instances, the NCO:active hydrogen ratio of the isocyanate to the active hydrogen compound will preferably fall within the same ranges as disclosed herein for the NCO:OH ratios.

Suitable polyols for use in preparing a composition of this invention include polyalkylene ethers derived from the condensation of alkylene oxides (e.g., ethylene oxide, propylene oxide, and blends thereof), as well as tetrahydrofuran based polytetramethylene ether glycols, polycaprolactone polyols, polycarbonate polyols and polyester polyols. Examples of suitable polyols include polytetrahydrofuran polyol ("PTHF", also known as polytetramethylene oxide ("PTMO") or polytetramethylene ether glycol ("PTMEG")

Preferably, the polyol component can be provided in the form of a blend of two or more different molecular weights selected from the commercially available group consisting of 250, 650, 1000, 1400, 2000, and 2900. Materials having different molecular weights can be blended, e.g., using between 10:1 and 1:10 equivalent weights of a lower and higher molecular weight component (e.g., 250 and 1000 MW components), respectively, and preferably between about 2:1 and about 1:2 equivalent weights. The optimal combination of components, as well as the absolute and relative proportions thereof, are selected to provide a polymer system that, upon mixing an/or heating, is sufficiently "flowable" under ambient or other selected controlled conditions (e.g., temperature) to permit it to be sterilized, mixed, delivered, and cured, e.g., using minimally invasive means, to provide the properties desired for in vivo applications as described herein.

A preferred polymer system of this invention also includes the use of one or more chain extenders. Suitable chain extenders for use in the present invention provide an optimal combination of such properties as hard segment molecular weight and molecular weight distribution, phase separation and domain formation, virtual cross-linking by hard segment domains. In cases in which more than two functional extenders are used, their combination also provides an optimal or desire level of chemical crosslinking between both hard segment chains and hard and soft segment chains.

An example of a particularly preferred chain extender is a combination of a linear (e.g., two-functional) chain extender, such as 1,4-butanediol ("BDO"), together with a cross-linking (e.g., tri- or higher-functional) chain extender such as trimethylol propane ("TMP"). Such chain extenders can be prepared in any suitable combination to produce a unique degree of cross-linking, predominantly in the hard segment domains but also crossing the phase boundaries.

Additional cross-linking in the hard segment augments the virtual cross-links generated by the hard segment domains and provides higher cross-link density and efficiency, resulting in the reinforcement of non cross-linked segments. This can be particularly useful in relatively soft polyurethanes, such as those suitable for the repair of damaged cartilage. Reinforcement by virtual cross-links alone may not generate sufficient strength for in vivo performance in certain applications. Additional cross-linking from the soft segment, potentially generated by use of higher functional polyols can be used to provide stiffer and less elastomeric materials. In this manner a balancing of hard and soft segments, and their relative contributions to overall properties can be achieved.

Additionally, a polymer system of the present invention preferably contains one or more, and more preferably two or more, biocompatible catalysts that can assist in controlling the curing process, including the following periods: (1) the induction period, (2) the setting period, and finally, (3) the final cure of the biomaterial. Together these three periods, including their absolute and relative lengths, and the rate of acceleration or cure within each period, determine the cure kinetics or profile.

The word "induction", and inflections thereof, when used in this respect refers to the time period between mixing or activation of one or more polymer components (under conditions suitable to begin the curing process), and the onset of gelation. In a method of the present invention, this period generally corresponds with the delivery of the biomaterial to the site of ultimate use. The induction period is characterized by infinitesimal or limited increase in viscosity of reacting mixture and relatively flat exotherm profile. Generally, a biomaterial of this invention is simultaneously mixed just prior to actual delivery into the joint site, providing the surgeon with sufficient time to add and position material (e.g., into anchor points) before gelation causes the material to become less easily workable. Thereafter, the surgeon can leave the material in place as it sets, e.g., for on the order of three to twenty minutes, before placing instruments back into the site to finish sculpting the implant, or performing other desired steps such as positioning the femoral condyles to shape the implant.

The term "set time" (or gel time), as used herein, is determined from the initial mixing of components, and refers to the time needed for a mixed and delivered system to set to the point where it can be shaped. This period is characterized by a rapid rise in the slope of the reaction exotherm at the end of the period. By the end of this period, the surface of the gelled biomaterial is preferably tack free and will allow shaping, e.g., by positioning of the condyles. The "cure time", as used herein, is determined from the initial mixing, and refers to the total time needed to mix, shape and fully cure the biomaterial to the desired extent under the conditions used. Preferred polymer systems of this invention preferably provide an induction period that ends within about thirty seconds to two minutes following mixing of the components, followed by a set time of about 3 to about 15 minutes following mixing.

During the curing process (including both setting and completion of cure) the polymer system preferably exhibits an exotherm compatible for its intended use, e.g., preferably an exotherm of less than about 70 to about 90 C., and more preferably less than about 80 C. Given the present description, those skilled in the art will appreciate the manner in which the polymer system can be adjusted in a variety of ways to obtain suitable exotherm, during setting and cure, e.g., by the use of temperature dependent synergistic catalysis. Catalysts suitable for use in compositions of the present invention provide an optimal combination of such properties as set time, cure time, and in turn, viscosity (and flowability) of the curing polymer system.

In a particularly preferred embodiment, the selection of catalyst and other ingredients provides a cure profile that exhibits both synergistic and "delayed action" kinetics, in which induction of cure begins immediately upon mixing the polymer components, and is relatively "flat" during the induction period, without significant increase of viscosity of reaction mixture. This period permits delivery of the "flowable" polymer to the tissue injury site, and is followed by a setting period characterized by variable increase in slope (in a plot of temperature vs. time) that is designed to quickly drive the curing process to completion, and in turn, to quickly provide a set polymer that is sufficiently strong and tack-free to permit final shaping.

Examples of suitable catalyts include tin compounds (such as tin esters, tin alkylesters, and tin mercaptides), amines, such as tertiary amines and the like. An example of a suitable catalyst system is a combination of a tin catalyst (e.g., "Cotin 222", available under the trademark "Cotin 222" from Cascam, Company, Bayonne N.J.) and a tertiary amine (e.g., DABCO(TEDA), a triethylene diamine catalyst available from Air Products, Allentown, Pa. These components can be used in any suitable ratio, e.g., between about 1:1 parts and about 1:5 parts of the tin catalyst and the diamine, respectively.

Other ingredients can be used as well, including different amine-based catalysts available to those in the art. Examples of optional ingredients include antioxidants, such as vitamin E, which can be used as a biocompatible antioxidant and mediator of macrophage attack designed to destroy the implant in vivo.

Other suitable ingredients include dyes, such as "Green GLS Dye" (available from Clarian Corp., Charlotte, N.C.) that can be added (e.g., at a concentration of about 0.01% to about 0.05%, by weight) to facilitate the ability to visualize the polymer in the course of delivery to the "repair" site. Preferred dyes are stable to change in the course of sterilization, e.g., by irradiation such as gamma or Electron-beam.

Optionally, inorganic fillers, such as calcium carbonate, titanium dioxide or barium sulfate can be added as well, in about 0.5 to about 20 percent (by weight) to affect the viscosity and thixotropic properties of the resultant mixture, to modify or increase the load bearing ability of the polymer and/or to render the implanted biomaterial radiopaque.

Preparation and Delivery

The composition of the present invention can be delivered and cured within the body, preferably by minimally invasive means. In one preferred embodiment, the composition is used to resurface or repair a joint, such as a knee or intervertebral disc. In another preferred embodiment, the composition is used to form an implant in situ, e.g., in the form of a catheter such as a stent, graft, or shunt.

Ingredients such as those provided herein can be combined in any suitable manner to provide a composition capable of being delivered to the injury site, preferably via minimally invasive means. In a preferred embodiment, the composition is provided as a system having a plurality of parts, e.g., a two-part system, wherein the two parts are capable of being separately prepared, sterilized, and packaged, such that the parts can be mixed in the operating room and at the time of use in order to initiate the curing process.

Compositions provided as a plurality of components, e.g., a two-part polyurethane system, can be mixed at the time of use using suitable mixing techniques, such as those commonly used for the delivery of two-part adhesive formulations. A suitable mixing device involves, for instance, a static mixer having a hollow tube having a segmented, helical vein running through its lumen. A two-part polyurethane system can be mixed by forcing the respective components through the lumen, under pressure. In addition, any mechanically driven mixing device or impingement mixing device are suitable to accomplish the mixing of a plurality of components.

In a further embodiment, the static mixer can be used in a system having an application cannula, an application tip, and a cartridge having two or more chambers, each containing a separate component of the composition system. A hand-powered, pneumatically, or electrically controlled extrusion gun can be used to extrude or eject the components through, for example, the static mixer, in order to completely mix them and thereby begin the process of curing. The composition system then flows through the cannula and to the joint site or surface through the application tip. The length, diameter, and vein design of the mixing element can be varied as necessary to achieve the desired mixing efficiency.

The composition of the present invention can be delivered to a site within the body, and there cured, preferably using minimally invasive means, in order to repair (e.g., reconstruct or resurface) tissue such as cartilage, and particularly cartilage associated with diarthroidal and amphiarthroidal joints. Optionally, the composition can be delivered and cured within an implanted mold device. Using minimally invasive means a composition can be delivered to a site within the body, e.g., to a mold or a site of damaged or diseased cartilage, to be cured in situ in order to provide an implant or repair the cartilage without undue surgical trauma.

In other aspects, the invention provides compositions, including polymer systems, useful for performing such a method, as well as methods of preparing and using such compositions. In yet further aspects, the invention provides a joint, e.g., a diarthroidal or amphiarthroidal joint, having interposed therein a composition that has been delivered and cured in situ.

Properties

Compositions of the present invention provide improvement in one or more of the following properties as compared to those previously known, without detrimental effect on other desirable properties described herein.

In a particularly preferred embodiment, Applicants have discovered a composition that provides significantly improved hardness and strength during stage (c) identified above, while also providing improved cure kinetics during stage (b), all without undue effect on other desirable properties. In its fully cured state, for instance, a suitable composition of the present invention provides a hardness of about 60 Shore to about 95 Shore, as determined by ASTM Test Method D2240 set forth herein. Optionally, and preferably in addition to such improved hardness, the fully cured composition provides improved tensile strength as well, as determined by ASTM Test Method D412 herein. For instance, a preferred composition of this invention provides a tensile strength (measured in the dry state) of about 6,000 psi to about 10,000 psi. The composition provides a "wet" tensile strength (e.g., as determined after soaking the sample in saline for one week) of about 3,000 psi to about 5,000 psi. As a further optional feature, a preferred composition of this invention provides a biphasic cure pattern, as depicted and described with respect to FIG. 1 herein.

Optionally, or preferably in addition to improved hardness, a preferred fully cured composition of this invention provides a tensile strength of about 6,000 psi to about 10,000 psi, as determined by ASTM Test Method D412 herein.

Accordingly, in a preferred embodiment, the present invention provides a curable polyurethane composition comprising a plurality of parts capable of being sterilized, stably stored, and mixed at the time of use in order to provide a flowable composition and to initiate cure, the parts including: (1) a quasi-prepolymer component comprising the reaction product of one or more polyether polyols, one or more isocyanates, and one or more reactive hydrophobic additives, and (2) a curative component comprising one or more polyether polyols, one or more chain extenders, and one or more catalysts.

More preferred is a composition as described above wherein the reactive hydrophobic additive comprises an hydroxyl- or amine-terminated polymer or copolymer selected from the group consisting of poybutadiene, polyisobutylene, silicone, polyisoprene, copolymers of butadiene with acryolnitrile, copolymers of butadiene with styrene, copolymers of isoprene with acrylonitrile, copolymers of isoprene with styrene, and mixtures thereof, and particularly preferred is a composition wherein the additive comprises hydroxyl-terminated polybutadiene. Within such a composition, the hydroxyl-terminated polybutadiene can be present at a concentration of between about 5% and about 20%, by weight, based on the weight of the composition, and more preferably between about 8% and about 15% by weight.

Also preferred is a composition as described herein wherein the polyether component is selected from the group consisting of linear or branched polyols with polyether backbones of polyoxyethylene, polyoxypropylene, and polyoxytetramethylene, and copolymers thereof, e.g., wherein the polyether component is present in the prepolymer component at a concentration of between about 2% and about 10% by weight, and is present in the curative component at a final concentration of between about 25% and 45%, based on the weight of the composition. An example of such a composition is one in which the polyether component comprises polytetramethylene oxide having a molecular weight in the range of 250 to 1000.

Further preferred is a composition which the isocyanate component comprises an aromatic isocyanate selected from the group consisting of 2,2'-, 2,4'-, and 4,4'-diphenylmethanediisocyanate, and combinations thereof, preferably where the isocyanate is present in excess in the prepolymer component, at a concentration of between about 30% and about 50% by weight, based on the weight of the composition.

In another aspect, the invention provides a curable polyurethane composition comprising a plurality of parts capable of being sterilized, stably stored, and mixed at the time of use in order to provide a flowable composition and to initiate cure, the parts including:

(1) a quasi-prepolymer component comprising the reaction product of
   (a) one or more polyether polyols selected from the group consisting of linear or branched polyols with polyether backbones of polyoxyethylene, polyoxypropylene, and polyoxytetramethylene, and copolymers thereof,
   (b) one or more isocyanates selected from the group consisting of 2,2'- , 2,4'- , and 4,4'-diphenylmethanediisocyanate (MDI), and combinations thereof, and
   (c) one or more reactive hydrophobic additives comprising hydroxyl- or amine-terminated compounds selected from the group consisting of poybutadiene, polyisobutylene, silicones, polyisoprene, copolymers of butadiene with acryolnitrile, copolymers of butadiene with styrene, copolymers of isoprene with acrylonitrile, copolymers of isoprene with styrene, and mixtures thereof, and (2) a curative component comprising
   (a) one or more polyether polyols as defined in part (1)(a),
   (b) a combination of linear and branched chain extenders, and
   (c) one or more catalysts.

Preferably the catalysts, in combination with the remaining components, are sufficient to permit the composition to cure upon mixing at physiological temperature with a cure profile that comprises sequentially an onset period, a gelation period, and a complete cure period.

In yet another aspect, the invention provides a cured polyurethane implant suitable for extended use in vivo, the implant being formed as the reaction product of a composition that comprises: (1) a quasi-prepolymer component comprising the reaction product of one or more polyether polyols, one or more isocyanates, and one or more reactive hydrophobic additives, and (2) a curative component comprising one or more polyether polyols, one or more chain extenders, and one or more catalysts. Such an implant exhibits improved Shore Hardness and tensile strength, as compared to an implant prepared from a comparable composition lacking hydrophobic additives, e.g., a Shore hardness of between about 60 and about 95 Shore, as determined by ASTM Test Method D2240, and a dry tensile strength of between about 6000 psi and about 10,000 psi, as determined by ASTM Test Method D412. The invention also provides such an implant according positioned in permanent or temporary contact with a joint surface in vivo, and preferably positioned in permanent contact with the surface of subchrondral bone in the knee joint.

The invention also provides a kit comprising a plurality of sterile, flowable parts capable of being mixed at the time of use in order to provide a flowable composition and to initiate cure, the parts including: (1) a quasi-prepolymer component comprising the reaction product of one or more polyether polyols, one or more isocyanates, and one or more reactive hydrophobic additives, and (2) a curative component comprising one or more polyether polyols, one or more chain extenders, and one or more catalysts. Preferably, the kit further comprises a delivery device for use in mixing the quasi-prepolymer component and curative component, and delivering the mixture to a tissue site using minimally invasive means.

Common polymeric materials for use in medical devices include, for example, polyvinyl chlorides, polyethylenes, stryrenic resins, polypropylene, thermoplastic polyesters, thermoplastic elastomers, polycarbonates, acrylonitrile-butadiene-styrene ("ABS") resins, acrylics, polyurethanes, nylons, styrene acrylonitriles, and cellulosics. See, for example, "Guide to Medical Plastics", pages 41–78 in *Medical Device & Diagnostic Industry*, April 1994, the disclosure of which is incorporated herein by reference.

Suitable matrix materials (i.e., biomaterials) for use in the present invention are those polymeric materials that provide an optimal combination of properties relating to their manufacture, application, and in vivo use. In the uncured state, such properties include processability and the ability to be stably sterilized and stored. In the course of applying such material, such properties include hydrogel compatibility and capacity, flowability, and in vivo curability. In the cured state, such properties include moldability, cured strength (e.g., tensile and compressive), elongation to break, and biocompatability. Examples of suitable matrix materials include, but are not limited to, silicone polymers and polyurethane polymers.

In a preferred embodiment, the biomaterial matrix is formed of a silicone polymer, i.e., polymer containing a repeating silicon-oxygen backbone together with organic R groups attached to a significant portion of the silicon atoms by silicon-carbon bonds. See generally, "Silicones", pages 1048–1059 in *Concise Encyclopedia of Polymer Science and Engineering*, Eds. Mark et al., Wiley and Sons, 1990, the disclosure of which is incorporated herein by reference.

Silicone polymers are commercially available in at least three general classes, namely as homopolymers, silicone random polymers, and silicone-organic (block) copolymers. Homopolymers in the form of polydimethyl siloxanes are preferred, and constitute the largest volume of homopolymers produced today.

In an alternative preferred embodiment, the biomaterial matrix is formed of a polyurethane polymer. Polyurethanes, e.g, thermoplastic polyurethanes ("TPU"), are typically prepared using three reactants: an isocyanate, a long-chain macrodiol, and a short-chain diol extender. The isocyanate and long-chain diol form a "soft" segment, while the isocyanate and short-chain diol form a "hard" segment. It is the interaction of soft and hard segments that determines and provide the polymer with rubber-like properties.

During melt processing, the polyurethane chains are linear and assume the configuration into which they are formed, such as by injection molding, or in the case of the present invention, by arthroscopic application. On cooling, the hard segments form ordered domains held together by hydrogen bonding. These domains act as cross-links to the linear chains, making the material similar to a cross-linked rubber.

Those skilled in the art, in view of the present invention, will appreciate the manner in which the choice of isocyanate, macrodiol, and chain extender can be varied to achieve a wide diversity of properties. Preferred TPU's for medical use are presently based on the use of a diisocyanate such as diphenylmethane diisocyanate ("MDI"), a glycol such as polytetramethylene ether glycol, and a diol such as 1,4-butanediol.

Natural cartilage is a non-vascular structure found in various parts of the body. The natural elasticity of articular cartilage enables it to break the force of concussions, while its smoothness affords ease and freedom of movement. In terms of thickness, cartilage tends to take on the shape of the articular surface on which it lies.

Preferred biomaterials, therefore, are intended to mimic many of the physical-chemical characteristics of natural cartilage. Biomaterials can be provided as one component systems, or as two or more component systems that can be mixed prior to or during delivery, or at the site of repair. Generally such biomaterials are flowable in their uncured form, meaning they are of sufficient viscosity to allow their delivery through a cannula of on the order of about 1 mm to about 6 mm inner diameter, and preferably of about 2 mm to about 3 mm inner diameter. Such biomaterials are also curable, meaning that they can be cured or otherwise modified, in situ, at the tissue site, in order to undergo a phase or chemical change sufficient to retain a desired position and configuration.

When cured, preferred materials can be homogeneous (i.e., providing the same chemical-physical parameters throughout), or they can be heterogeneous. An example of a heterogeneous biomaterial for use as a disc replacement is a biomaterial that mimics the natural disc by providing a more rigid outer envelope (akin to the annulus) and a more liquid (e.g, cushioning or softer) interior core (akin to the nucleus). In an alternative embodiment, biomaterials can be used that provide implants having varying regions of varying or different physical-chemical properties. With disc replacement, for instance, biomaterials can be used to provide a more rigid, annulus-like outer region, and a more fluid, nucleus-like core. Such di- or higher phasic cured materials can be prepared by the use of a single biomaterial, e.g., one that undergoes varying states of cure, or a plurality of biomaterials.

Common polymeric materials for use in medical devices include, for example, polyvinyl chlorides, polyethylenes, styrenic resins, polypropylene, thermoplastic polyesters, thermoplastic elastomers, polycarbonates, acrylonitrile-butadiene-styrene ("ABS") resins, acrylics, polyurethanes, nylons, styrene acrylonitriles, and cellulosics. See, for example, "Guide to Medical Plastics", pages 41–78 in *Medical Device & Diagnostic Industry*, April, 1994, the disclosure of which is incorporated herein by reference.

Suitable biomaterials for use in the present invention are those polymeric materials that provide an optimal combination of properties relating to their manufacture, application, and in vivo use. In the uncured state, such properties include processability, and the ability to be stably sterilized and stored. In the course of applying such material, such properties as flowability, moldability, and in vivo curability. In the cured state, such properties include cured strength (e.g., tensile and compressive), stiffness, biocompatability and biostability. Examples of suitable biomaterials include, but are not limited to, polyurethane polymers.

In a preferred embodiment, the biomaterial comprises a polyurethane polymer. Polyurethanes, e.g, thermoplastic polyurethanes ("TPU"), are typically prepared using three reactants: an isocyanate, a long-chain macrodiol, and a short-chain diol extender. The isocyanate and long-chain diol form a "soft" segment, while the isocyanate and short-chain diol form a "hard" segment. The hard segments form ordered domains held together by hydrogen bonding. These domains act as cross-links to the linear chains, making the material similar to a cross-linked rubber. It is the interaction of soft and hard segments that determines and provides the polymer with rubber-like properties.

Those skilled in the art, in view of the present invention, will appreciate the manner in which the choice of isocyanate, macrodiol, and chain extender can be varied to achieve a wide array of properties. Preferred TPU's for medical use are presently based on the use of a diisocyanate such as diphenylmethane diisocyanate ("MDI"), a glycol such as polytetramethylene ether glycol, and a diol such as 1,4-butanediol.

Biomaterials of the present invention can also include other optional adjuvants and additives, such as stabilizers, fillers, antioxidants, catalysts, plasticizers, pigments, and lubricants, to the extent such optional ingredients do not diminish the utility of the composition for its intended purpose.

When cured, the biomaterials demonstrate an optimal combination of physical/chemical properties, particularly in terms of their conformational stability, dissolution stability, biocompatability, and physical performance, e.g., physical properties such as density, thickness, and surface roughness, and mechanical properties such as load-bearing strength, tensile strength, shear strength, fatigue, impact absorption, wear characteristics, and surface abrasion. Such performance can be evaluated using procedures commonly accepted for the evaluation of natural tissue and joints, as well as the evaluation of biomaterials.

In particular, preferred biomaterials, in the cured form, exhibit mechanical properties that approximate those of the natural tissue that they are intended to replace. For instance, for load bearing applications, preferred cured composites exhibit a load bearing strength of between about 50 and about 500 psi (pounds per square inch), preferably between about 100 and about 300 psi, and more preferably between about 100 and 200 psi. Such composites also exhibit a shear stress of between about 10 and 100 psi, and preferably between about 30 and 50 psi, as such units are typically determined in the evaluation of natural tissue and joints. Such composites also exhibit a tensile strength of between about 3500 and about 6000 psi, and preferably between about 4000 and about 5000 psi, using test methods generally available to those skilled in the art, for instance using an "Instron" tensile tester.

Preferred biomaterials are also stable under conditions used for sterilization, and additionally are stable on storage and in the course of delivery. They are also capable of flowing through a delivery cannula to an in vivo location, and being cured in situ, as by exposure to an energy source such as ultraviolet light or by chemical reaction. Thereafter the cured biomaterial is suitably amenable to shaping and contouring, by the use of conventional or custom designed arthroscopic tools or instruments. Over the course of their use in the body the cured, contoured biomaterial exhibits physical-chemical properties suitable for use in extended in vivo applications.

In a preferred embodiment, the biomaterial is a polyurethane provided as a two-part prepolymer system comprising a diisocyanate, a polyalkylene oxide and low molecular diols as chain extenders. The final polymer having a hard segment content of about 25 to about 50% by weight, and preferably of about 30 to about 40% by weight, based on the weight of the diisocyanate and chain extender. Optionally, and preferably, one or more catalysts are incorporated into one or more components of the biomaterial, in order to cure the biomaterial in the physiological environment within a desired length of time. Preferably, biomaterials of the present invention are able to cure (i.e., to the point where distraction means can be removed and/or other biomaterial added), within on the order of 5 minutes or less, and more preferably within on the order of 3 minutes or less.

Preferably, means are employed to improve the biostability, i.e., the oxidative and/or hydrolytic stability, of the biomaterial in vivo, thereby extending the life of the implant. See, for instance, A. Takahara, et al., "Effect of Soft Segment Chemistry on the Biostability of Segmented Polyurethanes. I. In vitro Oxidation", *J. Biomedical Materials Research,* 25:341–356 (1991) and A. Takahara, et al., "Effect of Soft Segment Chemistry on the Biostability of Segmented Polyurethanes. II. In vitro Hydrolytic Degradation and Lipid Sorption", *J. Biomedical Materials Research,* 26:801–818 (1992), the disclosures of both of which are incorporated herein by reference.

Suitable means for improving biostability include the use of an aliphatic macrodiol such as hydrogenated polybutadiene (HPDI). By judicious choice of the corresponding diisocyanate (e.g., MDI) and chain extender (e.g., ethylenediamine), those skilled in the art will be able to achieve the desired packing density, or crystallinity, of the hard segments, thereby improving the hydrolytic stability of the cured polyurethane.

Biomaterials provided as a plurality of components, e.g., a two-part polyurethane system, can be mixed at the time of use using suitable mixing techniques, such as those commonly used for the delivery of two-part adhesive formulations. A suitable mixing device involves, for instance, a static mixer having a hollow tube having a segmented, helical vein running through its lumen. A two-part polyurethane system can be mixed by forcing the respective components through the lumen, under pressure.

In a further embodiment, the static mixer can be used in a system having an application cannula, an application tip, and a cartridge having two or more chambers, each containing a separate component of the biomaterial system. A hand-powered or electrically controlled extrusion gun can be used to extrude the components through the static mixer, in order to completely mix them and thereby begin the process of curing. The biomaterial system then flows through the cannula and to the joint site or surface through the application tip. The length, diameter, and vein design of the mixing element can be varied as necessary to achieve the desired mixing efficiency.

Hydrogels suitable for use in composites of the present invention are water-containing gels, i.e., polymers characterized by hydrophilicity and insolubility in water. See, for instance, "Hydrogels", pages 458–459 in *Concise Encyclopedia of Polymer Science and Engineering,* Eds. Mark et al., Wiley and Sons, 1990, the disclosure of which is incorporated herein by reference. Although their use is optional in the present invention, the inclusion of hydrogels is highly preferred since they tend to contribute a number of desirable qualities. By virtue of their hydrophilic, water-containing nature, hydrogels assist the cured composite with load bearing capabilities of the cured composite. They also tend to decrease frictional forces on the composite and add thermal elasticity.

In a preferred embodiment, the hydrogel is a fine, powdery synthetic hydrogel. Suitable hydrogels exhibit an optimal combination of such properties as compatibility with the matrix polymer of choice, and biocompatability.

Suitable hydrogels swell to an equilibrium volume in water, but preserve their shape. Synthetic hydrogels suitable for use in forming a composite of the present invention include those based on methacrylic and acrylic esters, (meth)acrylamide hydrogels, and those based on N-vinyl-2-pyrrolidinone.

Preferred hydrogels include those formed from monomeric hydroxyalkyl acrylates and methacrylates, copolymerized with a suitable cross-linking agent, such as ethylene dimethacrylate ("EDMA").

In a particularly preferred embodiment the matrix polymer is a siloxane (i.e., silicone polymer), and preferably one selected from the group consisting of alpha, omega-dihydroxypoly(dimethylsiloxane) and poly(dimethylsiloxane) with 0.2 mol % of vinylmethyl-siloxane units. Dispersed as the hydrogel component in the preferred polymer is 15% to 30% (by weight based on the weight of the uncured composite) of a lightly cross-linked hydrogel aggregate. A preferred hydrogel aggregate is formed by 2-hydroxyethyl methacrylate (HEMA) cross-linked by ethylene dimethacrylate (EDMA) at a concentration of 2%–5% by weight, based on the weight of the hydrogel.

Those skilled in the art will appreciate the manner in which hydrogel/matrix combinations and concentrations can be altered based on their intended application. For instance, a stiffer composite with a low hydrogel concentration, e.g., ~10% based on the final weight of the composite, would be suitable for intervertebral disc replacement.

Depending, for instance, on their intended application, biomaterials will preferably contain a hydrogel phase at a concentration of between about 15 and 50 weight percent, and preferably between about 10 and about 50 weight percent, and preferably between about 15 and about 30 weight percent, based on the weight of the combination of matrix and hydrogel.

Composites of the present invention can also include other optional adjuvants and additives, such as stabilizers, fillers, antioxidants, catalysts, plasticizers, pigments, and lubricants, to the extent such optional ingredients do not diminish the utility of the composition for its intended purpose.

Cured polymer-hydrogel composites demonstrate an optimal combination of physical/chemical properties, particularly in terms of their conformational stability, dissolution stability, biocompatability, and physical performance, e.g., physical properties such as density, thickness, and surface roughness, and mechanical properties such as load-bearing strength, tensile strength, static shear strength, fatigue of the anchor points, impact absorption, wear characteristics, and surface abrasion. Such performance can be evaluated using procedures commonly accepted for the evaluation of natural tissue and joints, as well as the evaluation of biomaterials.

In particular, preferred composite materials, in the cured form, exhibit mechanical properties approximating those of the natural tissue that they are intended to replace. For instance, preferred cured composites exhibit a load bearing strength of between about 50 and about 200 psi (pounds per square inch), and preferably between about 100 and about 150 psi. Such composites also exhibit a shear stress of between about 10 and 100 psi, and preferably between about 30 and 50 psi, as such units are typically determined in the evaluation of natural tissue and joints.

Preferred biomaterials are also stable under conditions used for sterilization, and additionally are stable on storage and in the course of delivery. They are also capable of flowing through a delivery cannula to an in vivo location, and being cured in situ, as by exposure to an energy source such as ultraviolet light or by chemical reaction. Thereafter the cured biomaterial is suitably amenable to shaping and contouring, by the use of conventional or custom designed arthroscopic tools or instruments. Over the course of their use in the body the cured, contoured biomaterial exhibits physical-chemical properties suitable for use in extended in vivo applications.

Suitable biomaterials for use in a method of this invention include, but are not limited to, those described in Applicant's co-pending PCT Application Nos. PCT/US97/00457. Biomaterials can be provided as one component systems, or as two or more component systems that can be mixed prior to or during delivery, or at the site of repair. Generally such biomaterials are flowable in their uncured form, meaning they are of sufficient viscosity to allow their delivery through a cannula of on the order of about 2 mm to about 6 mm inner diameter, and preferably of about 3 mm to about 5 mm inner diameter. Such biomaterials are also curable, meaning that they can be cured or otherwise modified, in situ, at the tissue site, in order to undergo a phase or chemical change sufficient to retain a desired position and configuration.

Preferred biomaterials, therefore, are intended to mimic many of the physical-chemical characteristics of natural tissue. When cured, preferred materials can be homogeneous (i.e., providing the same chemical-physical parameters throughout), or they can be heterogeneous. An example of a heterogeneous biomaterial for use as a disc replacement is a biomaterial that mimics the natural disc by providing a more rigid outer envelope (akin to the annulus) and a more liquid (e.g., cushioning or softer) interior core (akin to the nucleus).

Suitable biomaterials for use in the present invention are those polymeric materials that provide an optimal combination of properties relating to their manufacture, application, and in vivo use. In the uncured state, such properties include processability, and the ability to be stably sterilized and stored. In the course of applying such material, such properties as flowability, moldability, and in vivo curability. In the cured state, such properties include cured strength (e.g., tensile and compressive), stiffness, biocompatability and biostability. Examples of suitable biomaterials include, but are not limited to, polyurethane polymers.

Biomaterials of the present invention can also include other optional adjuvants and additives, such as stabilizers, fillers, antioxidants, catalysts, plasticizers, pigments, and lubricants, to the extent such optional ingredients do not diminish the utility of the composition for its intended purpose.

In particular, preferred biomaterials, in the cured form, exhibit mechanical properties that approximate those of the natural tissue that they are intended to replace. For instance, for load bearing applications, preferred cured composites exhibit a load bearing strength of between about 50 and about 500 psi (pounds per square inch), and preferably between about 100 and about 200 psi. Such composites also exhibit a shear stress of between about 10 and 100 psi, and preferably between about 30 and 50 psi, as such units are typically determined in the evaluation of natural tissue and joints. Such composites further exhibit a tensile strength of between about 4,000 psi and about 10,000 psi, and preferably between about 6,000 psi and about 8,000 psi. Cured biomaterials for use in non-orthopedic applications, e.g., as catheters, can generally exhibit strength and stress parameters that are appreciably lower than those used in more demanding applications.

Preferred biomaterials are also stable under conditions used for sterilization, and additionally are stable on storage and in the course of delivery. They are also capable of flowing through a delivery conduit to an in vivo location, and being cured in situ, as by exposure to an energy source such as ultraviolet light or by chemical reaction. Thereafter the cured biomaterial is suitably amenable to shaping and contouring, by the use of conventional or custom designed arthroscopic tools or instruments. Over the course of their use in the body the cured, contoured biomaterial exhibits physical-chemical properties suitable for use in extended in vivo applications.

As described above, a biomaterial composition of the present invention can be provided in a heterogeneous form, e.g., having two or more portions that independently provide one or more properties that differ between the portions. For example, the present teaching can be employed in the following manner to provide a joint resurfacing implant having improved anchoring and tear resistance. Reactive liquid polyurethanes, as described above, can be mixed during delivery and polymerized in situ and in vivo in order resurface or restore damaged body joint. Commonly, and as also described herein, such an implant can be immobilized in the joint by means of one or more anchoring holes drilled into the implant site. Biomaterials having a surface hardness of about 65 to about 85 Shore A, are relatively soft, and can be used to simulate the cushioning properties of articulating cartilage they target to replace.

In certain applications it will be particularly desirable that the implant be even more firmly and permanently immobilized within the joint, in order to resist a "carpeting effect" that can otherwise be caused by load forces as well as frictional and/or twisting movements typical in the joint. Such an effect can serve to create extensive wear on the implant, leading to premature failure of the implant and even dislodging of the implant itself or portions thereof.

Given the present description, those skilled in the art will be able to determine the best manner to avoid such displacement, on a joint by joint and case by case basis. Suitable approaches can include, for instance, adjusting the size, shape, number and/or position of anchor points to be drilled in order to ensure optimal performance. Similarly, given the present description those skilled in the art will be able to determine the optimal biomaterial composition for use in a particular application, e.g., one that is sufficiently hard to avoid being "pulled out" of the anchoring holes under the expected prolonged use in vivo.

Compositions described herein can be made with an optimal combination of hardness, stiffness and strength, in order to resist deformation. Such properties, in turn, will permit the anchor points to better resist deformation, or failure. In turn, such biomaterials can provide improved immobilization of the implant, patient healing, and joint acceptance and performance. Harder implants, however, tend to experience significantly greater wear when introduced between surfaces of communicating or articulating bones.

Optionally, and preferably therefore, in order to provide an optimal combination of both stability and cushioning, the implant can be provided in the form of a heterogeneous composition, including a harder portion for use as anchor points, and a softer portion for cushioning. In an alternative embodiment, a multiphasic bulk morphology of the implant can be produced using an Interpenetrating Polymer Network (IPN), by bringing together softer and harder polymer networks while being polymerized.

In an alternative, and preferred embodiment, the present invention therefore provides a in situ formed composite that provides an optimal combination of anchoring and cushioning properties considered valuable for implant performance.

The respective portions of such a composite can be provided in any suitable form, for instance in a sandwich form, such as in the following manner:

1. A thin layer (e.g., about 0.01 mm to about 1.0 mm) of strong, stiff and tough polyurethane, having the surface hardness of 55–75 Shore D is deposited into the lesion, filling completely the anchoring holes. This layer is preferably either solid or microcellular, neat or enhanced with all potentially available biologicals to augment integration and immobilization into the surrounding environment; e.g. bone, cartilage, synovium, etc. Predominantly, however, the anchoring is improved by increased resistance to deformation and thus the "pullout", stemming from the harder and stiffer material. Aspects of biodurability vs. biodegradation can be considered for this anchoring layer. Given the present teaching, those skilled in the art will be able to provide suitable formulations to fulfill these needs.

2. Immediately after this first layer is deposited, the second layer, in the form of a softer, cartilage-like polyurethane, is delivered and formed over the anchoring layer to form the composite. This softer layer provides the functional requirements of the joint restoring implant.

The in vitro performance of such a combination has been evaluated in a wear simulator, using simulated body environment (lactated ringer solution/37 deg C.). Under a specified load and motion conditions, when immobilized in cross-linked polyurethane foam simulating the cancellous bone, the double-layered composite of harder/softer material failed to tear at 320,000–380,000 cycles. The single-layered sample of the current material and current approach has failed this test at approximately 20,000 cycles. These and other results and observations confirm that such an approach is capable of providing marked improvement.

In a related aspect, the system described herein can be used to provide a joint implant having a mushroom-like appearance, in which "head" represents the implant; the "stem" represents the anchoring system. Such an implant will flow with the force-field acting upon it to extend its durability in the joint, and is particularly useful for indications where the necessary lesion as taught in U.S. Pat. No 5,556,429 is impractical or impossible.

Reactive liquid polyurethanes, mixed during delivery and polymerized in situ and in vivo are used to resurface or restore damaged body joint as described herein. The in situ polymerized implant, based on polyurethanes having the surface hardness between 60–95 Shore A, is immobilized in the joint, in the prepared lesion, via drilled anchoring holes in the selected implant site. Anchoring holes are drilled at the "periphery" of the lesion. At least three holes are drilled to anchor the implant. As described above, such biomaterials are relatively soft, and are designed to simulate the properties of articulating cartilage they target to replace. Furthermore, these materials provide cushioning effect between respective bones of the respective joint.

As described above, and in order to avoid the "carpeting effect", it is often necessary that anchor holes be drilled, essentially conical in shape and placed in a staggered pattern, to be filled with curable biomaterial and become an integral part of the implant. It is difficult to drill the holes in "toe-nail" fashion with the bottom tip of the hole pointing toward the periphery of the lesion. This diminishes the "holding" power of the anchoring hole system. Similarly, increasing numbers of anchor holes can serve to weaken the bone surface plateau (e.g. tibial plateau of the knee joint) causing potential "cave in" of the tibial plateau under the load. Holes can also serve to retain whatever folds might be brought on in the course of a carpeting effect, thereby potentially accelerating implant failure.

In order to address such a situation, a preferred method includes the following steps:

1. A single, conically-shaped and center-located anchoring hole is drilled or otherwise generated within the joint surface to be restored.
2. A thin layer of 0.01 mm to 1.0 mm of strong, stiff and tough polyurethane, having the surface hardness of about 55 to about 75 Shore D is delivered to the plateau surface or the lesion, filling completely the anchoring hole, in order to generate the "stem" of the "mushroom". This stem layer can be provided in any suitable form, e.g., solid, microcellular, neat or enhanced with one or more biologicals to augment integration and immobilization into the surrounding environment; e.g. bone, cartilage, synovium, etc. Predominantly, however, the anchoring will be improved by increased resistance to deformation and thus the "pullout", stemming from the harder and stiffer material.
3. During or after delivery of the first layer, a second layer is delivered, e.g., in the form of a softer, cartilage-like polyurethane, which forms over the anchoring layer to form the composite in the form of "the head" of the "mushroom". Optionally, one or more layers can be delivered, in any suitable order and using any suitable materials, in order to provide a multi-layered stem and/or head.
4. Preferably, both the head and stem, and each layer therein, are provided in the form of a single material (e.g., polyurethane) in a manner that permits delivered in a single or multi-layered fashion.

The improved performance of such a composition has been verified in vitro, in a wear simulator, utilizing simulated body environment (lactated ringer solution/37 deg C.). Under a specified load and motion conditions, when immobilized in cross-linked polyurethane foam simulating the cancellous bone, the double-layered composite of harder/softer materials failed to tear at 320,000–380,000 cycles. The single layered sample of the current material and current approach has failed this test at approximately 20,000 cycles.

Mold Apparatus

In a preferred embodiment, the method of the invention involves an initial step of providing an implantable mold apparatus comprising a cavity adapted to receive and contain a flowable biomaterial and a conduit adapted to connect the cavity to a source of curable, flowable biomaterial. A cavity can take any suitable form, e.g., a unitary balloon-like cavity capable of being partially or completely filled with biomaterial in order to provide an intact prosthesis, or a shell-like or tubular cavity used to form a corresponding tubular prostheses. The mold can be of any suitable shape or dimension, and can itself include a plurality of cavities and/or other chambers or conduits, such as those suitable for the delivery of air or vacuum, as described herein.

The method can be used for a variety of applications, including for instance, for the preparation of an integral prostheses, e.g., for use in articulating joint repair or replacement and intervertebral disc repair. Alternatively, the method can be used to provide a hollow mold, such as a tubular mold for use in preparing implanted passageways, e.g., in the form of catheters, such as stents, shunts, or grafts.

In one preferred embodiment, the method of the invention is used in the course of intervertebral discectomy. In an amphiarthroidal joint such as the lumbar joint of the back, the vertebra are separated by an intervertebral disc formed of cartilage. Applicant's copending PCT Application No. PCT/US97/00457 (the entirety of which is incorporated herein by reference), inter alia, describes a method for repairing an intervertebral disc that comprises the steps of:

a) using microsurgical techniques to perform a discectomy while preserving an outer annular shell,
b) providing one or more curable biomaterials to the interior of the annular shell, and
c) curing the biomaterials in order to provide a replacement disc.

In a preferred embodiment, the distraction of the disc space is accomplished by the use of suitable distraction means, such as an inflatable balloon or bladder. The balloon can be delivered in deflated form to the interior of the annulus and there inflated, as by the delivery of biomaterial, in order to distract the disc space and retain the biomaterial.

An improved inflatable device for used in intervertebral disc repair will be described with reference to the Drawing, and in particular FIGS. 1 through 4. In FIG. 1, an apparatus (10) is shown having balloon portion (12) and biomaterial conduit (14). The balloon is dimensioned to be positioned within the annular shell following discectomy, and there filled with biomaterial in order to provide a replacement disc.

As shown, in a preferred embodiment, conduit (14) includes a venting system (16) that includes air passageway (18) passing from a distal point along the conduit, into and through its wall (20) in order to pass along the interior of the conduit. Air passageway (18) terminates at a point at or near the proximal end of balloon (12), where it can be used to provide gas under pressure (e.g.,in order to position the balloon and/or distract the joint) and where it can optionally be used to vent gas (e.g., air) within the balloon as the balloon is filled with biomaterial. As shown, the air passageway (18) is preferably provided with one or more vent holes (22) at locations within the balloon, which serve to facilitate the delivery of biomaterial by improving venting of gas from within the balloon. Conduit (14), including the air passageway, can be severed from balloon portion at or near the point (24) where they attach to or pass through the wall of the balloon. In this manner the conduit can be removed from the balloon as or after the biomaterial cures.

Figure 2:
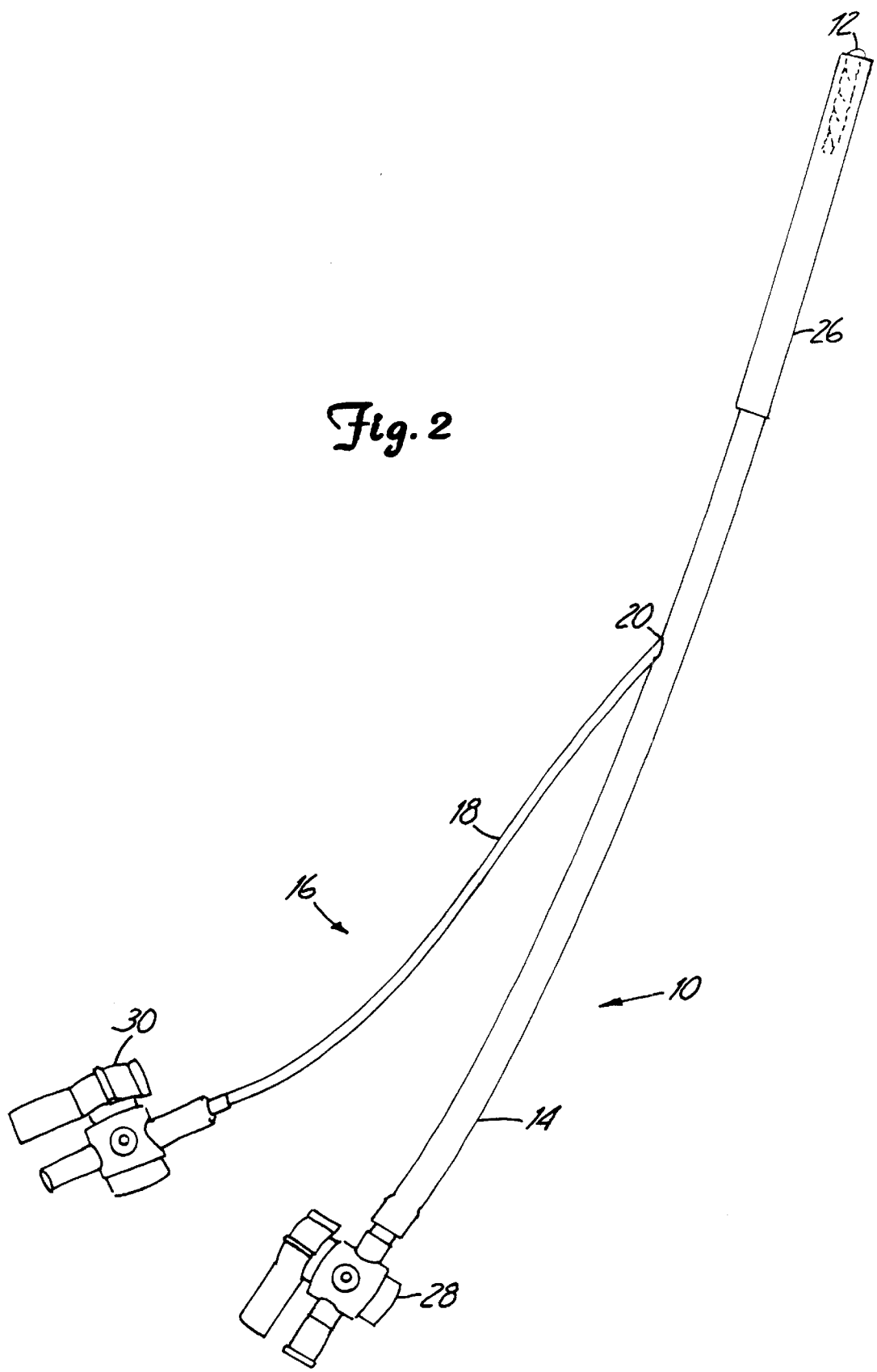
FIG. 2 shows the apparatus of FIG. 1 with the balloon in its collapsed form contained within an outer sheath, suitable for insertion and positioning within the disc space.

As shown in FIG. 2, the balloon is preferably provided in a form collapsed or rolled within sheath (26), which can be drawn back in situ in order to release the balloon. Sheath (26), conduit (14) and air passageway (18) can each prepared from materials commonly used for such purposes, such as polyurethane catheters, and suitably dimensioned to provide the respective functions. The conduit portion, for instance, will preferably be about 10 cm to about 30 cm in length, more preferably between about 15 cm to about 25 cm in length, and about 0.1 cm to about 10 cm, and more preferably about 0.3 cm to about 0.7 cm in outer diameter. The air passageway, in contrast, will typically be about 1 mm to about 3 mm in outer diameter, and of sufficient length to extend about 2 cm to about 4 cm beyond the proximal end of the conduit (and therefore into the balloon). The balloon, in turn, will typically be about 2 cm to about 3 cm in its longest dimension, about 1.5 cm to about 2.5 cm in width, and about 0.5 cm to about 1.5 cm in thickness, once filled with biomaterial. Both the biomaterial conduit (14) and air passageway (18) are preferably provided with controllable and adjustable valves (28) and (30), for use in adjusting the flow of biomaterial and gas, respectively, between the two.

Optionally, air passageway (18) can be provided such that it terminates at point substantially at or near where it meets the balloon, i.e., such that it does not extend into the balloon itself. In this manner it has been found that the balloon can still be adequately evacuated, yet in a manner that avoids the need to keep the distal portion of the air passageway permanently encased in cured biomaterial within the implant.

In a related embodiment, the mold apparatus, or a kit that contains or is adapted for use with such a mold apparatus, can include means for positioning the balloon in situ, e.g., in the form of a vascular guide wire that can be placed through the delivery conduit itself, or preferably through an air passageway that terminates at or near the point of contact with the balloon. The guide wire can be designed to substantially assume the curved contour of the extended but unfilled balloon, and to provide a plane of orientation, in order to both facilitate placement of the balloon and provide an outline of the periphery of the balloon in position and prior to filling. Thereafter the guide wire can be removed from the site prior to delivery of the biomaterial and air evacuation. The use of a guide wire in this manner is particularly facilitated by the use of an air passageway that is unconnected to, and positioned outside of, the biomaterial conduit.

Optionally, and in order to facilitate the placement and storage of the collapsed balloon within a sheath, the invention further provides a rod, e.g., a plastic core material, dimensioned to be placed within the balloon, preferably by extending the rod through the conduit. Once in place, a vacuum can be drawn on the balloon through the air passageway in order to collapse the balloon around the rod. Simultaneously, the balloon can also be twisted or otherwise positioned into a desired conformation to facilitate a particular desired unfolding pattern when later inflated or filled with biomaterial. Provided the user has, or is provided with, a suitable vacuum source, the step of collapsing the balloon in this manner can be accomplished at any suitable time, including just prior to use. In certain embodiments it will be desirable to collapse the balloon just prior to its use, e.g., when using balloon materials that may tend to stick together or lose structural integrity over the course of extended storage in a collapsed form. Alternatively, such balloon materials can be provided with a suitable surface coating, e.g., a covalently bound polymeric coating, in order to improve the lubricity of the surface and thereby minimize the chance that contacting balloon surfaces will adhere to each other.

Mold cavities of the present invention, e.g., the balloon of FIG. 1, can be formed by any suitable means. In a preferred embodiment, the balloon is fabricated by dipcoating a suitably shaped mandrel into a curable polymer solution. Applicants have discovered that a mandrel ideally suited for this purpose can be prepared from a remoldable bismuth-based material. Examples of suitable materials include low melting point fusible materials, such as bismuth alloys that are commercially available from a number of sources (e.g., as Part nos. E-LMA-117, 158, 255 and 281 from Small Parts, Inc. Miami Lakes, Fla.). Such an alloy, for instance, begins to melt at about 117 degrees C., and solidifies at room temperature, expanding slightly in the process of cooling. The allow can be melted out in hot water and collected for re-use.

Figure 3:
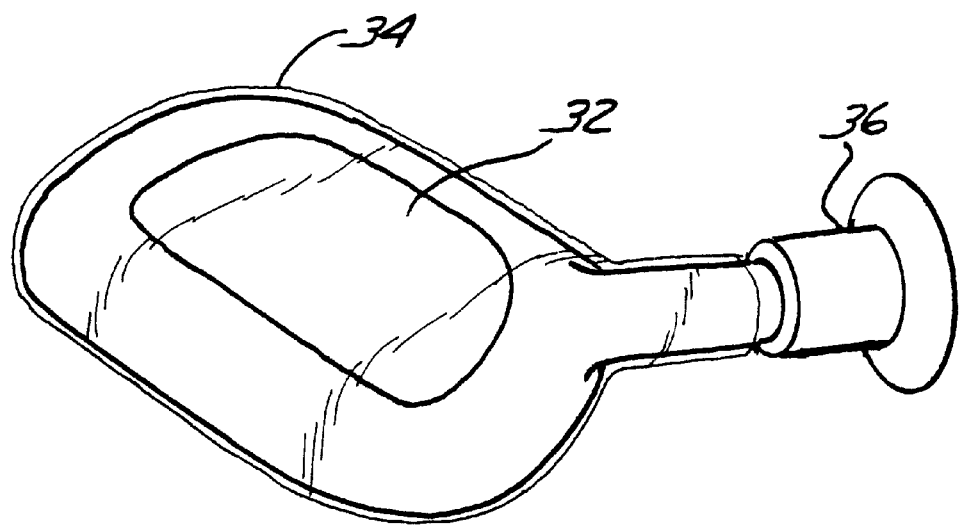
FIG. 3 shows a mandrel used for forming the balloon of FIG. 1 by dip-coating the mandrel in a suitable solution of curable polymer.
Figure 4:
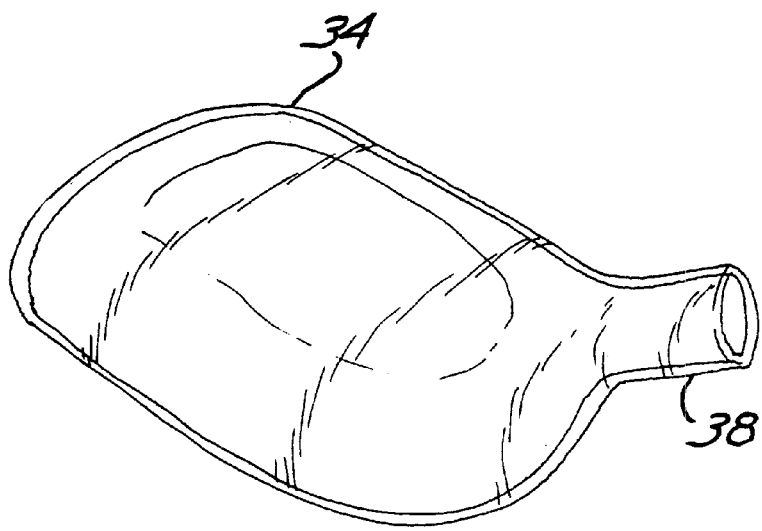
FIG. 4 shows a balloon as formed upon the mandrel shown in FIG. 3

A preferred mandrel will be described with reference to FIGS. 3 and 4. FIG. 3 shows a mandrel (32) covered with newly formed balloon (34) and held in chuck (36). The solid mandrel (32) is used to form a balloon by dipcoating it in a suitable solution (not shown) as described herein. Once cast, the mandrel can be melted in order to remove it from the balloon by dipping the combination in water at about 120 degrees C. for about 5 to 15 minutes. As the mandrel liquifies it can be poured and/or squeezed out of the balloon and reformed for further use. FIG. 4 shows the resultant balloon (34), after removal of the mandrel, formed by this process. In the preferred embodiment shown, the balloon retains an integral stem portion (38) that provides an attachment site for the conduit shown in FIG. 1.

A preferred balloon provides an optimal combination of such properties as extendibility and strength. In this respect, a balloon that is substantially non-extendible, but strong, can be used to distract the disc space upon delivery of biomaterial, and by virtue of the biomaterial delivery pressure. Preferred materials for use in preparing balloons of the present invention include, for instance, block copolymers such as castable thermoplastic polyurethanes, for instance those available under the tradenames ESTANE (Goodrich), PELLETHANE (Dow), TEXIN (Bayer), Roylar (Uniroyal), and ELASTOTHANE (Thiocol), as well as castable linear polyurethane ureas, such as those available under the tradenames CHROMOFLEX AR (Cardiotech), BIONATE (Polymer Technology Group), and BIOMER (Thoratec).

Preferred elastomeric polymers provide an optimal combination of such properties as flexibility under static and dynamic conditions, strength, tensile strength, elongation, elastic modulus during cyclic deformation, ductility, stability and durability, compliance, porosity, and patency. See generally, M. Szycher, J. Biomater. Appl. "Biostability of polyurethane elastomers: a critical review", 3(2):297–402 (1988); A. Coury, et al., "Factors and interactions affecting the performance of polyurethane elastomers in medical devices", J. Biomater. Appl. 3(2):130–179 (1988); and Pavlova M, et al., "Biocompatible and biodegradable polyurethane polymers", Biomaterials 14(13):1024–1029 (1993), the disclosures of which are incorporated herein by reference.

Given the present description those skilled in the art will be able to employ conventional methods, such as casting, for forming balloons and similar molds of this invention. See, for instance, "Casting", pp. 109–110, in *Concise Encyclopedia of Polymer Science and Engineering*, Kroschwitz, ed., John Wiley & Sons (1990). In a preferred embodiment, a remoldable bismuth mandrel is formed having desired shape and dimensions. Balloons can be cast to achieve any desired final thickness, preferably on the order of 0.005 inches (0.01 cm) to about 0.015 (0.05 cm) inches thick, and preferably between about 0.008 inches (0.02 cm) to about 0.012 inches (0.03 cm). The balloon itself is preferably cleaned, e.g., by the use of suitable solvents.

Optionally, and preferably, reinforcing materials such as meshes formed of natural or synthetic materials can be incorporated into the balloon, e.g., by layering them onto various portions while still wet, and covering the mesh with subsequent dip coats. A mesh can be cut in a form sufficient to extend around the perimeter of the balloon, for instance, in order to provide added strength in the course of filling the balloon and distracting the space. Suitable materials for preparing meshes include polyamide (e.g., NYLON), polyester (e.g., tradenames DACRON and HYTREL), polyethylene, and polypropylene, as well as liquid crystal polymers available under the tradename VECTRA.

The various components of a mold apparatus can be prepared and assembled using techniques within the skill of those in the related art. For instance, a balloon, conduit and air passageway can be individually prepared and assembled by attaching the balloon to an end of the conduit, e.g., by gluing or sonic welding, and positioning the air passageway within or alongside the conduit and extending into the balloon. Thereafter the sheath can be applied to the conduit and slid over the balloon in its collapsed or rolled configuration. Other materials or means can be incorporated into the apparatus, such as radioopaque portions, to facilitate the surgeons ability to orient the balloon in situ. Also, various joints and junctures between the parts of the apparatus can be sealed by the use of suitable adhesives or other materials.

Figure 5:
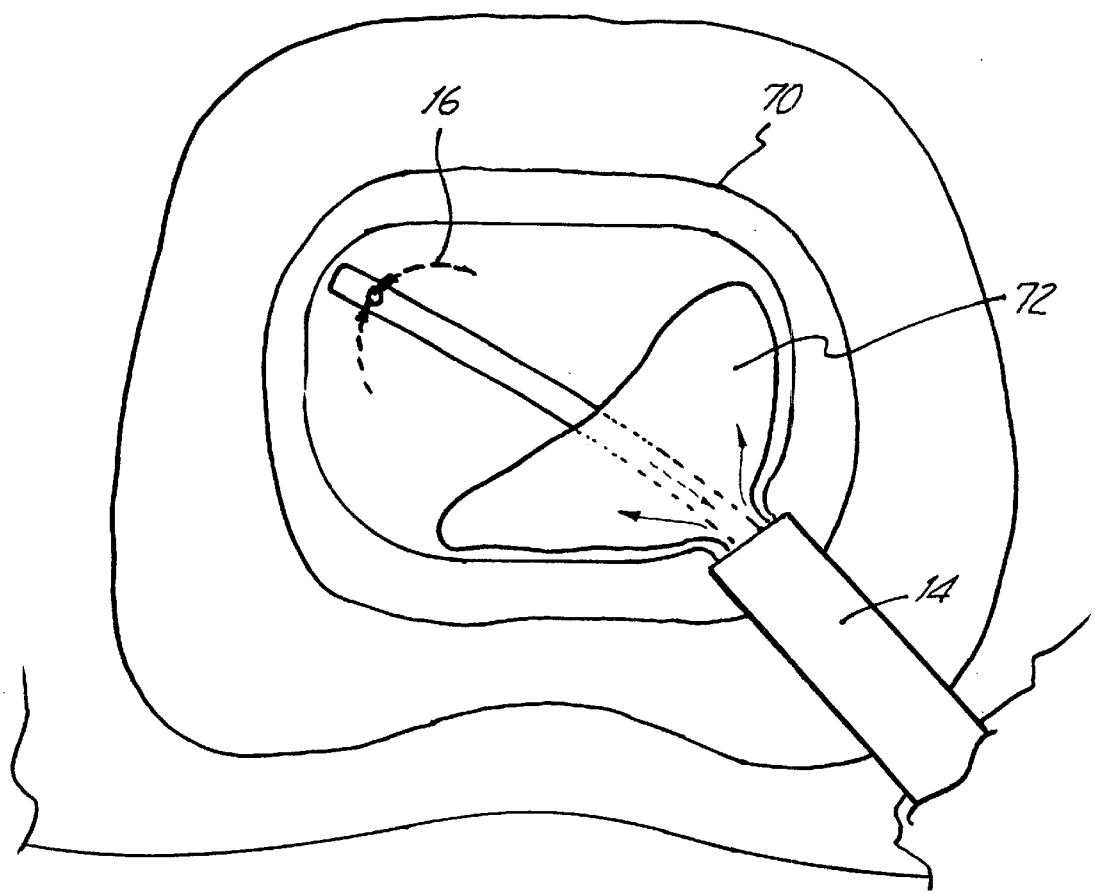
FIG. 5 shows the balloon of FIG. 1 positioned within the disc space and in the course of filling with biomaterial.

The use of a preferred mold apparatus will be described with reference to FIG. 5, which shows the balloon portion (12) in place, with sheath (26) retracted, within a reamed annular shell (70). A curable biomaterial (72) is delivered into the balloon at the same time that air is withdrawn from the balloon through vent holes (22) of air passageway (18). In use, and with the balloon positioned within the sheath, the apparatus can be inserted into the body through minimally invasive means in order to position the proximal end at the site of intended use, e.g., within the disc space. Once positioned, the sheath can be withdrawn in order to release the balloon. Optionally, air or other suitable gas can be delivered to the balloon through the air passageway in order to position the balloon and/or distract the joint. Thereafter, the valve can be opened to begin the flow of curable biomaterial. As biomaterial enters the balloon, gas in the balloon can be vented through air passageway by drawing a slight vacuum on the distal end of the passageway, as by the use of a syringe or other suitable vacuum source. The biomaterial continues to fill the balloon, which in turn serves to distract (or assist in distracting) the space, until desired dimensions are obtained, whereupon the flow of biomaterial is stopped, the biomaterial is allowed to continue to fully cure (harden), and the balloon severed from the conduit.

The method and apparatus of the invention can also be used to repair other joints, including diarthroidal and amphiarthroidal joints. Examples of suitable diarthroidal joints include the ginglymus (a hinge joint, as in the interphalangeal joints and the joint between the humerus and the ulna); throchoides (a pivot joint, as in superior radio-ulnar articulation and atlanto-axial joint); condyloid (ovoid head with elliptical cavity, as in the wrist joint); reciprocal reception (saddle joint formed of convex and concave surfaces, as in the carpo-metacarpal joint of the thumb); enarthrosis (ball and socket joint, as in the hip and shoulder joints) and arthrodia (gliding joint, as in the carpal and tarsal articulations).

Figure 6:
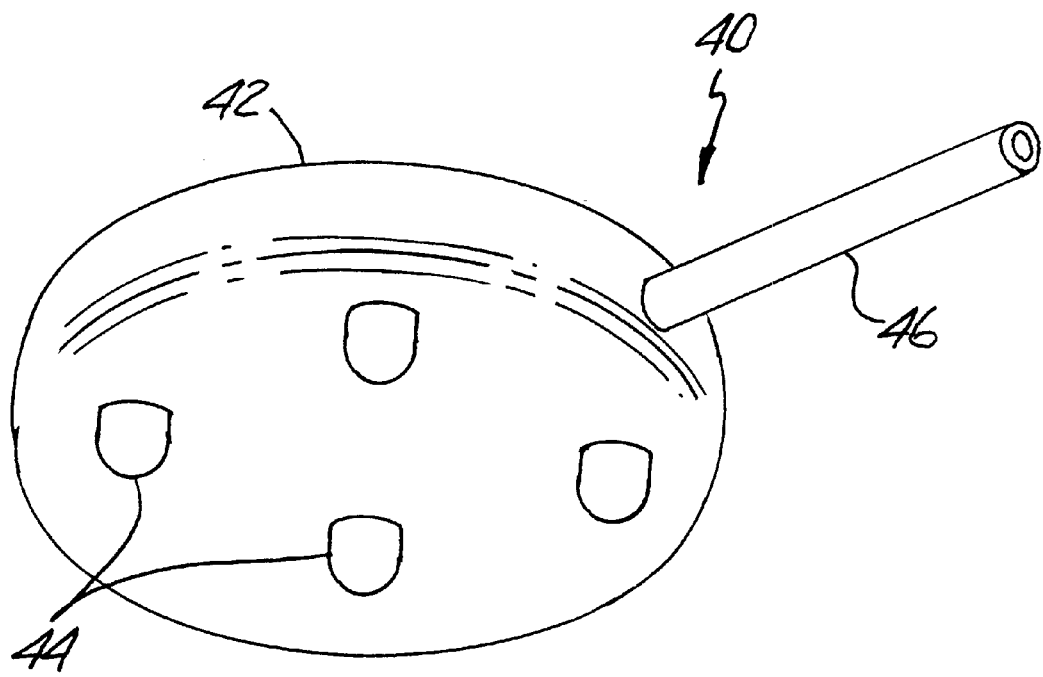
FIG. 6 shows a preferred embodiment of a mold apparatus for use in the repair or replacement of knee cartilage.
Figure 7:
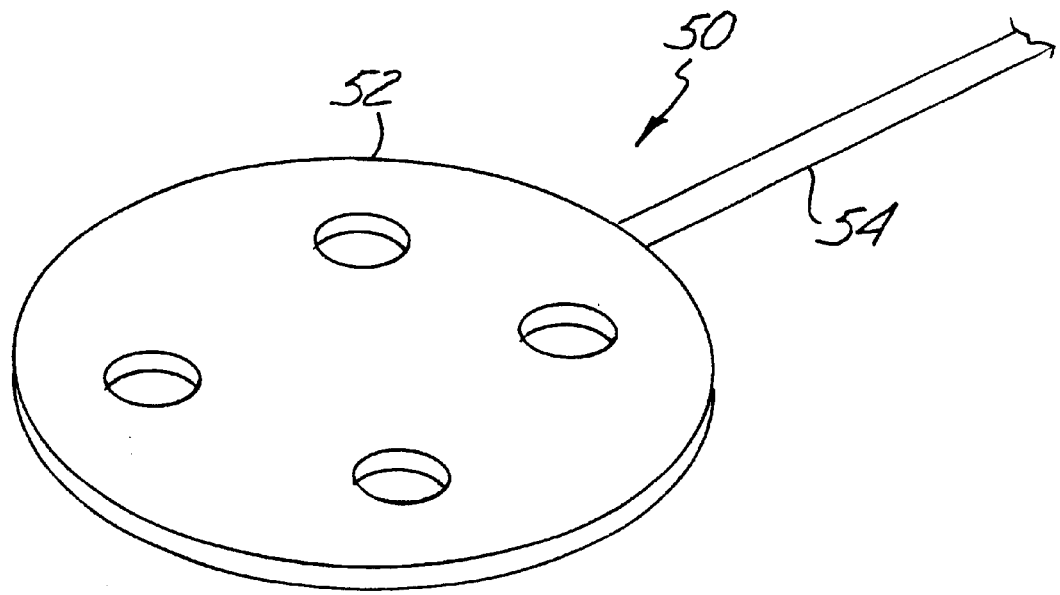
FIG. 7 shows a drilling template for use in connection with the apparatus of FIG. 6.

In a preferred embodiment, the method and apparatus are employed to repair the knee joint. FIGS. 6 and 7, for instance, show a preferred balloon for use in knee surgery. As seen in FIG. 6, the mold (40) includes a generally ovoid inflatable portion (42), preferably having protruding foot portions (44) extending therefrom and flowably attached to biomaterial conduit (46). In use, the foot portions, or footpads, (44) can be implanted into corresponding anchor sites drilled into the bone, in order to provide improved attachment thereto.

As seen in FIG. 7, in a further preferred embodiment the present invention further provides a template (50) for use in drilling the holes that will correspond with foot portions (44). As shown, template (50) includes both a substantially planar, disc-like, template portion (52) and an extendable delivery probe (54) useful for positioning the template by minimally invasive means. The disc portion, in turn, is provided with one or more, and preferably several apertures of predetermined spacing and diameter, to correspond with the foot portions of a corresponding inflatable portion. A template such as that shown is considered novel in its own right, and particularly in the context of a system in which a mold and template are packaged or paired together to facilitate the delivery and placement of the mold in situ.

One or more footpads are formed or formable in a manner integral with the balloon or are attached thereto in any suitable manner. The footpads can themselves be solid, or can be part of the cavity and filled with biomaterial. The footpads are dimensioned to be positioned into corresponding anchor points within the bone, to further secure the mold to the site of tissue injury. Optionally, or in addition to the use of footpads, the underside of the balloon may have multiple fenestrations (e.g., micro holes) sufficient to permit the biomaterial to traverse the barrier of the balloon in order to contact the subchondral bone and/or fill the anchor points. The apparatus can also be provided with means, such as a colinear air lumen or other means sufficient to evacuate the balloon in the course of biomaterial delivery, thereby facilitating the process further.

Optionally, and also preferably, the cavity provided by an apparatus of this invention can be in a form sufficient to provide a hollow, e.g., tubular biomaterial upon cure. As such, the apparatus can be used to form an internal passageway, for instance, to support (internally or externally) an existing passageway (such as a vessel), to provide a replacement for natural vessel, and/or to provide a new passageway such as a shunt, between areas not previously or naturally connected.

A tubular mold can be used to form a catheter, which in turn, can serve as a prosthethic device for a variety of applications. A catheter of the present invention can take a variety of forms, including, for instance, as an angiographic catheter, ureteral catheter, central venous catheter, eustachian catheter, bladder catheter, intracardiac catheter, pacing catheter, and prostatic catheter.

A catheter of this invention can also serve as a shunt, to provide a diversion or bypass of accumulations of fluid to an absorbing or excreting system. Suitable applications include, for instance, the use of a catheter as an arteriovenous shunt, Blalock shunt (subclavian artery to pulmonary artery), cavopulmonary shunt, distal splenorenal shunt, jejunoileal shunt, "left-to-right" shunt (e.g., in the heart as through a septal defect, or from the systemic circulation to the pulmonary), mesocaval shunt, peritoneovenous shunt, portacaval shunt, portasystemic shunt, renal-splenic shunt, "right-to-left" shunt (e.g., in the heart as through a septal defect, or from the pulmonary artery into the aorta), Scribner shunt (artery, generally radial, to cephalic vein), splenorenal shunt (including a "Warren" distal splenorenal shunt), ventriculocisternal shunt, transjugular intrahepatic portosystemic shunt, and a Waterston shunt (ascending aorta and subjacent right pulmonary artery).

Similarly, the catheter can be used to form a graft for abdominal aortic aneurysms, and in micro form as a graft for cerebral aneurysms.

In yet a further preferred embodiment, a mold of this invention can be used to prepare a solid (e.g., curved and/or straight) rod, such as a medullary rod for internal fixation of various fractures. The balloon, and in turn rod, can also be placed by minimally invasive means.

For use as a stent-like prosthesis, a catheter of this invention can be used in a variety of applications. In yet another aspect the invention provides a stent formed by a method of the present invention. Stents of the present invention can be used in a variety of applications, including for peripheral vasculature, abdominal aortic aneurysms, and applications in connection with the prostate, esophagus, trachea, bile or biliary tract, and intestine. A stent of this invention can lay within the lumen of a tubular structure to provide support during or after anastomosis, or to assure patency of an intact but contracted lumen.

The construction and use of a tubular apparatus of the present invention will be further described with reference to the Drawing. A preferred embodiment is shown in FIGS. 8 and 9, wherein the former depicts the apparatus in its uninflated and unfilled form, and the latter depicts the apparatus of FIG. 8 in its inflated and filled condition. As seen in both Figures, apparatus (60) comprises an inner fluid passageway (62), surrounded by a generally concentric and inflatable air chamber (64), the air chamber being surrounded by a generally concentric and sealed or sealable biomaterial cavity (66). The fluid passageway is adapted to permit the flow of a bodily fluid such as blood in the course of insertion and delivery of the apparatus. The air chamber is adapted for attachment to a source of positive or negative air pressure, and the biomaterial chamber is adapted to be attached to a source of flowable biomaterial which can be cured in situ to form a tubular prosthetic implant such as a catheter. Optionally, means can be provided to vent or evacuate the biomaterial chamber in the course of filling with biomaterial, e.g., by the application of slight vacuum using a separate and additional lumen (not shown).

As can be seen by reference to FIG. 10, the fluid passageway (62) and air chamber (64) are separated by a first barrier (68), while air chamber (64) and biomaterial cavity (66) are separated by a second barrier (70). Outermost wall (72) provides the external surface of the biomaterial cavity and generally serves as an outer wall of the apparatus. Along its length, fluid passageway is sufficiently long to permit it to be delivered to a desired site within the body. The air chamber and biomaterial cavity, in turn, are provided along a portion of the fluid passageway, and generally need only be sufficiently long to serve their purpose in the preparation of a prosthetic implant.

In use, the air chamber can be inflated with air (or other suitable material) to a desired position and dimensions, whereupon the biomaterial can be delivered to fill the biomaterial cavity and cured in situ to form an implanted catheter. Optionally, the air chamber can be inflated before, during and/or after delivery and/or cure of the biomaterial. Thereafter the air chamber can be deflated and, together with the fluid passageway, removed from the body leaving the cured biomaterial in place as a catheter.

Optionally also, a mold apparatus of the type shown in FIG. 10 can be provided with means for venting the biomaterial chamber, e.g., in the course of filling that chamber with biomaterial. Venting means can be provided in a manner analogous to that described above with respect to the intervertebral disc balloon, that is, by the use of a separate air passageway operably attached to the biomaterial chamber on its proximal end, and attached or attachable to a vacuum source or source of pressurized air (or gas) on its opposite end.

The cross-sectional view provided in FIG. 10 demonstrates the manner in which fluid passageway (62) serves to permit the continued flow of fluid within the body in the course of use. Adjacent or surrounding the passageway is one or more air passageways (64) that can be used to inflate biomaterial cavity (66) and establish it in a desired position with respect to the body and the passageway.

In another preferred embodiment, the present invention provides a method for forming a prosthesis in situ, the method comprising the steps of:

a) providing a mold apparatus comprising an inner fluid passageway, a portion of the passageway being surrounded by a circumferential inflatable air chamber, a portion of the air chamber being surrounded by a circumferential biomaterial cavity, the fluid passageway being adapted to permit the flow of a bodily fluid or substance in the course of insertion and delivery of the catheter, the air chamber being adapted for operable attachment to a source of positive or negative air pressure, and the biomaterial chamber being adapted for operable attachment to a source of flowable, curable biomaterial which can be cured in situ to form a catheter, wherein the air chamber, upon inflation serves to define the inner dimensions of the catheter, and upon deflation allows free separation and removal of the passageway and air chamber, leaving the newly formed biomaterial prosthesis in place, b) inserting the apparatus to a desired point within the body, c) applying positive air pressure to inflate the air chamber to a desired dimension, d) filling the biomaterial cavity with biomaterial with the apparatus maintained in its inflated position, d) curing the biomaterial, and e) deflating and withdrawing the apparatus in a manner that leaves the cured biomaterial in situ, to serve as an implanted prosthesis.

In another embodiment, the invention provides a mold apparatus comprising a inner fluid passageway, a portion of which is surrounded by a circumferential, radially expansible, and inflatable air chamber, a portion of the air chamber being surrounded by a circumferential, radially expansible, biomaterial cavity, the fluid passageway being adapted to permit the flow of bodily fluid or substances in the course of insertion and delivery of the catheter, the air chamber being adapted for operable attachment to a source of positive or negative air pressure, and the biomaterial chamber being adapted to be flowably attached to a source of biomaterial which can be cured in situ to form an implanted prosthesis.

In an alternative embodiment, the biomaterial passageway can itself be contoured or shaped in any suitable manner, e.g., to provide a helical or spiral flow path along the length of the mold apparatus, e.g., in order to provide improved control over the flow of biomaterial and/or to provide improved dimensional stability to the cured implant. Similarly, the biomaterial passageway can be branched or segmented in any suitable fashion, e.g., to provide a "Y" shaped configuration to accommodate vascular branch points such as that of the aorta.

The fluid passageway of this embodiment can be provided by any material suitable to provide an optimal combination of such properties as nontoxicity, the ability to be bonded or otherwise attached to the material(s) used to form the air chamber and/or biomaterial cavity. An example of a suitable material for forming the fluid passageway is polyethylene. The air chamber and biomaterial can be formed from any suitable material, or combination of materials. Optionally, and preferably, the air chamber will be formed having, as its interior surface, the exterior surface of the fluid passageway. The remaining surface of the air chamber is preferably fabricated from a different, and expandable, material capable of being sealed to the passageway at its ends, and contacting and expanding the dimensions of the biomaterial cavity upon inflation. The outer wall of the fluid passageway, therefore, is preferably of sufficient strength to maintain its patency and integrity in order to withstand the pressure used to inflate the air chamber.

The biomaterial cavity, in turn, can similarly share a common wall (its interior) with the exterior wall of the air chamber, particularly if measures are taken to ensure that desired portions of the apparatus can be withdrawn from the cured biomaterial in a manner that permits the cured biomaterial to remain within the body. Optionally, and preferably, the barrier between the air chamber and biomaterial cavity is formed of two or more layers, one serving as the exterior, and expandable, wall of the air chamber, and the other laying substantially adjacent that wall and serving as the interior wall of the biomaterial cavity, and in turn, of the implanted prosthetic. In an alternative embodiment, the outer and inner walls of the biomaterial cavity can themselves be integrally attached (e.g., tacked) together in a spiral configuration in order to strengthen the cylindrical geometry and facilitate both the evacuation of air and biomaterial delivery.

The walls of the fluid passageway, air chamber and biomaterial cavity are each of suitable dimensions (e.g., thickness and length) for their intended purpose. Generally the walls of the fluid passageway will be on the order of 0.02 inches (about 0.05 cm) or less in thickness, with the outer walls of the chamber and cavity being appreciably thinner, e.g., on the order of 0.01 inches (about 0.02 cm) or less and 0.005 inches (about 0.01 cm) or less, respectively. In such an embodiment, it is the walls of the fluid passageway that provide with apparatus with much, if not all, of the necessary strength and rigidity for insertion and use.

The overall diameter of the fluid passageway can be adapted to its desired purpose, but is generally between about 0.1 cm and about 3 cm, and preferably between about 0.2 cm and about 2 cm. The diameters of the air chamber and biomaterial cavity, in turn, can also be adapted to their desired purpose, but will generally be between about 0.5 cm and about 5 cm (and preferably between about 1 cm and about 3 cm) for the overall diameter of the inflated air chamber and filled biomaterial cavity. In turn, the biomaterial cavity can be used to form an implanted catheter of any suitable inner and outer diameter, with a corresponding wall thickness of between about 0.1 mm and about 5 mm, and preferably between about 0.5 mm and about 2 mm. In its uninflated and unfilled condition the diameter of the entire assembly is generally less than that of the vessel into which it will be inserted.

Those skilled in the art, given the present description, will appreciate that the various materials and/or portions used to fabricate such an apparatus can be secured in any suitable fashion, e.g., by the use of appropriate medical-grade adhesives, by the use of multiple wraps of fine thread or suture, by heat sealing, sonic welding, and the like. Generally, the fluid passageway will be provided in the form of a cylindrical body, having the air chamber and biomaterial cavity similarly formed and positioned as cylindrical and concentric bodies, with the chamber configured to taper down at its ends for attachment to the outer surface of the fluid passageway, and the biomaterial cavity also tapered down at its ends for attachment to the outer surface of the air chamber.

In a particularly preferred embodiment, and as shown in FIGS. 8 and 9, at least two lumens are mounted as integral parts of the catheter body, including an air lumen (74) and a biomaterial lumen (76). The air lumen is connected to an inflation port that passes through the outside wall and into the air chamber. The opposite end of the air lumen passes along the distal length of the catheter to be controllably connected to an air or vacuum source. The biomaterial lumen is flowably connected to an inflation port that passes through the outside wall and into the biomaterial cavity, with its opposite end passing along the distal length of the catheter to be controllably connected to a biomaterial source.

Preferably with the apparatus in its uninflated and unfilled condition, the apparatus is dimensioned to be delivered through minimally invasive means to a desired position within the body. The inflatable air chamber and tillable biomaterial cavity can both be stored and inserted in a collapsed condition adjacent the outside surface of the fluid passageway. Optionally, the apparatus can be covered by a removable sheath (not shown) or other means suitable to facilitate its delivery to the desired position.

In use, the apparatus can be inserted through minimally invasive means through an artery or other bodily vessel to a desired point within the body, for instance, to a stenosed region of a blood vessel. Once in place, positive air pressure is applied in order to inflate the air chamber to a desired dimension. In the course of inflating the air chamber the outer and surrounding biomaterial cavity is suitably positioned for the receipt of biomaterial. As biomaterial fills the cavity, the pressure in the air chamber can be reduced in order to accommodate the increasing pressure and volume of biomaterial. Once the biomaterial cavity is filled to the desired extent, the air pressure can be further reduced in the air chamber, to the point where a vacuum can be drawn if desired, and the delivery conduit (fluid passageway and deflated air chamber) can be removed from the site. Ideally, the outer wall of the air chamber is distinct from the inner wall of the biomaterial cavity, such that the air chamber can be readily separated from the filled cavity, and axially removed therefrom.

Suitable materials for preparing a mold apparatus of the present invention are those that are presently used for such purposes as balloon angioplasty. Suitable materials provide an optimal combination of such properties as compliance, biostability and biocompatability, and mechanical characteristics such as elasticity and strength. A mold apparatus can be provided in any suitable form, including having a plurality of layers and/or a plurality of compartments when expanded. A useful apparatus will include the balloon or other biomaterial cavity itself, together with a delivery catheter (optionally having a plurality of lumen extending longitudinally therewith), and fluid or gas pressure delivery means.

In each embodiment, it is possible to treat or otherwise adapt the outer, tissue contacting, surface of the mold in a manner that facilitates its use. For instance, mold material can be rendered porous or fenestrated in order to permit it to become saturated with the biomaterial and/or to permit tissue to growth into the material or attach itself thereto. Optionally, and also preferably, the mold material can be chemically or biochemically treated, e.g., coated, to enhance the function or prevent unwanted interactions with the surrounding biological environment. Suitable coatings can be used, for instance, to render the mold material lubricious, biocompatible. Such coatings can be attached in any suitable manner, e.g., covalently attached or passively adsorbed, and in a manner that is either permanent in nature or slowly releasable or replaceable over time.

Although the present invention has been described with reference to the structures disclosed herein, it is not confined to the details set forth and this application is intended to cover any and all modifications and changes as may come within the scope of the following claims.

As another step of the method of the invention, the tissue injury site is prepared for receipt of the biomaterial. Those skilled in the art will appreciate the manner in which computer analysis of subchondral bone mass can allow the operator to customize the mechanical properties of the polymer-hydrogel composite to match the adjacent subchondral bone. This can be accomplished by adjusting the size of the hydrogel aggregates and by changing the percentage of the hydrogel in the polymer composite.

In a preferred method, the patient is first prepped and draped as per routine arthroscopic procedure. The first area to by resurfaced is then positioned horizontally and facing upright. If the opposing bone requires resurfacing the joint can be repositioned after the initial application has cured. This will allow gravity to assist in filling the anchor points and distributing the liquid composite evenly over the surface to be covered. Based on the present description, all the necessary maneuvers will typically be carried out using only two or three access portals.

The surface to be bonded is first cleaned of inflammatory synovia and frayed or damaged cartilage using a laser knife and/or other instruments, such as an arthroscopic shaver. The surface is then be prepared in order to improve its ability to accept and retain biomaterial. For instance, the subchondral bone is roughened by a burr and any osteophytes removed, also by the use of a burr. The bone is then irrigated to remove debris and the site suctioned dry. The bone can also be abraded in order to roughen its surface, or it can be coated with a suitable cement or other interface material.

In a preferred embodiment, anchoring points are created in the supporting joint tissue. For instance, inverted pyramidal or inverted T-shaped (Å) anchor points can be cut into the subchondral bone using specially designed arthroscopic drill bits or by laser means.

If only a small patch is needed only one or two anchor points may be sufficient, providing the number and arrangement of points is sufficient to prevent rotational or translational movement of the cured biomaterial.

If a larger area of cartilage is being replaced, then six to nine anchor points may be necessary. The number, size and location of sites can be determined on a case by case basis, by balancing the need to retain the cured biomaterial in permanent engagement with the natural tissue, with the need to avoid undue trauma or damage to the structural integrity of the natural tissue itself. Additional or other means, for instance the use of cements, can also be used to enhance the permanent engagement of the cured biomaterial with the natural joint tissue.

For instance, the prepared bone surface, including the anchor sites, can be treated with high molecular weight hyaluronic acid. This will improve adhesion of the polymer and act to inhibit inflammation and local osteoporosis. High molecular weight hyaluronic acid has also been shown to be an effective stimulator of osteophytes (i.e., bone-forming cells) as well as an inhibitor of Interleukin-1 (IL-1). As an IL-1 inhibitor, the acid will tend to decrease the inflammatory response in the area around the new insert.

As another step of the invention, a desired quantity of the curable biomaterial is delivered by minimally invasive means to the prepared site. Uncured biomaterial, either in bulk or in the form of separate reactive components, can be stored in suitable storage containers, e.g., sterile, teflon-lined metal canisters. The biomaterial can be delivered, as with a pump, from a storage canister to the delivery cannula on demand. Biomaterial can be delivered in the form of a single composition, e.g., including both polymer matrix and hydrogel, or can be delivered in the form of a plurality of components or ingredients. For instance, polymer matrix and hydrogel can be separately stored and suitably mixed or combined either in the course of delivery or at the injury site itself.

An example of a delivery system that can serve as a model for the delivery of uncured biomaterials is one presently sold by Dyonics, Inc. as the "InteliJET Fluid Management System". This system involves the a low pressure, high flow rate delivery of saline to a site, and combines delivery with suction that is automatically adjusted to specific blade styles.

In terms of its component parts, a preferred delivery system of the present invention will typically include a motor drive unit, with a remote controller, associated tube sets, a nonscope inflow delivery cannula, having independent fluid dynamics pressure and flow rate adjustments, an energy source for curing, attachments for the flush, vacuum, waste canister, overflow jars.

The application cannula will then be inserted into the joint and under visualization from the fiberoptic scope the polymer composite will be applied to the subchondral bone. The flow of the liquid phase polymer composite will be controlled by the operator via a foot pedal connected to the pumping mechanism on the polymer canister. The liquid phase polymer composite will flow from the tip of the application catheter to fill the anchor points and subsequently cover the subchondral bone.

As another step of the invention, the delivered biomaterial is cured by minimally invasive means and in such a manner that the cured biomaterial is retained in apposition to the prepared site. As described herein, the biomaterial can be cured by any suitable means, either in a single step or in stages as it is delivered. Preferred biomaterials are curable by the application of ultraviolet light, making them particularly amenable to a system that delivers such light by minimally invasive means.

When a sufficient amount of uncured biopolymer has been delivered, polymerization can be initiated by any suitable means, e.g., by the use of an ultraviolet light source at the tip of the application cannula. After the composite has cured (polymerized) the surface can be contoured as needed by other arthroscopic instruments. The joint will then be irrigated and the instruments removed from the portals.

Using the preferred composite materials described herein it is envisioned that there may be some natural migration of the hydrogel component to the composite surface in the course of curing. This migration will tend to produce a net positive charge across the surface of the composite. This positive charge, in turn, will tend to bind negatively charged hyaluronic acid, which is a compound that naturally occurs in the joint (produced by Type A synoviocytes). While not intending to be bound by theory, it would appear that the result of such binding will produce a lubricating effect to the surface of the composite. Since the hyaluronic acid is a normal product of the synovial lining cell it will be continuously replenished. A synthetic hydrophilic bilayer may alternatively be applied to reduce the coefficient of friction further.

The steps of preparing the joint surface and contouring the cured biomaterial, as described herein, can be accomplished using conventional arthroscopic instruments and tools. Stryker, Inc., Zimmer, Inc. and Dyonics, Inc. for instance, produce a wide array of arthroscopic surgical blades and instruments. Representative products are described in Dyonics' U.S. Pat. Nos. 4,274,414, 4,203,444, 4,705,038, 4,842,578, 4,834,729, and 4,983,179, the disclosure of each of which is incorporated herein by reference.

In yet another step of the present invention, the cured, retained biomaterial is contoured to achieve a desired conformation approximating that of natural tissue.

The preferred composite is heat moldable, allowing for sculpting with a probe that can be introduced through an arthroscopic portal. Such a probe will typically have a retractable, flat spatula-shaped end. The tip of the spatula can be heated to about 100 degrees centigrade, at which temperature the surface of the composite can be sculpted to the desired contour. As the composite cools, it will have sufficient memory to retain the shape it was given.

If unusual wear occurs in a given area, the implant can later be resculpted to cover the worn area without the need to repeat the entire process described above. Instead, the heat probe can simply be re-inserted under the arthroscopic visualization and the insert remolded to provide adequate size or properties in the needed area.

The steps described herein can be performed or combined in any suitable fashion. For instance, it is contemplated that the delivery, curing and contouring of biomaterial can be accomplished simultaneously and in a single step, for instance, by the use of a mold that retains a biomaterial in a desired shape as it is delivered and cured.

Optionally, and preferably, the final biomaterial can be subjected to further physical/chemical modifications, e.g., in order to enhance it performance, biocompatability, and the like. For instance, calcitonin and inflammatory inhibiting molecules such as Interleuken I inhibitors can be attached to the bone composite surface to prevent local osteoporosis and local inflammatory response which cause loosening. Similarly, the surface of the cured composite can optionally be modified in order to reduce the coefficient of friction.

In a preferred embodiment, a computer program can be used that is based on existing and ideal articulation angles. The program can assist the operator in producing a component having an optimal combination of physical characteristics, for instance contour and thickness, in order to provide optimal alignment of the involved joint.

Similarly, a holographic image can be generated through the arthroscope to aid the operator in producing the optimal thickness and contour of the polymer composite. Small joint applications, e.g., for wrists and ankles, as well as for metacarpal phalangeal joints, proximal interphalangeal joints, metatarsal phalangeal joints, and first carpalmetacarpal joints can also be developed.

What is claimed is:

1. A method for repairing a tissue site, the method comprising three steps of:
    (a) providing a sterile curable polyurethane biomaterial composition comprising a plurality of parts adapted to be mixed at the time of use in order to provide a flowable composition and to initiate cure,
    (b) mixing the composition parts in order to initiate cure and delivering a quantity of the curing composition to the tissue site, and
    (c) completely curing the delivered composition to provide a permanent repair of the tissue site,
    wherein the composition is sufficiently flowable to permit it to be delivered to the tissue site by minimally invasive means and there undergo complete cure in situ under physiologically acceptable conditions in order to provide a biocompatible material, wherein upon mixing the biomaterial sets within about 3 to about 15 minutes and when cured exhibits a tensile strength of between about 6,000 psi and about 10,000 psi when measured in the dry state according to ASTM test method D412.

2. A method according to claim 1 wherein the composition parts comprise: (1) a quasi-prepolymer component comprising the reaction product of one or more polyols, one or more isocyanates, and one or more reactive hydrophobic additives, and (2) a curative component comprising one or more polyols, one or more chain extenders, and one or more catalysts, and the composition provides improved cure characteristics and cured properties as compared to a comparable composition lacking the reactive hydrophobic additive component.

3. A method according to claim 2 wherein the improved cure characteristics include a significant reduction in the appearance of bubbles when cured in the presence of moisture.

4. A method according to claim 1 wherein the curing composition provides an surface exotherm of between about 50 and about 80 C.

5. A method according to claim 1 wherein the method is used to repair an orthopedic joint selected from the group consisting of diarthroidal and amphiarthroidal joints.

6. A method according to claim 5 wherein the amphiarthroidal joints are selected from the group consisting of synphysoidal joints and syndemoidal joints.

7. A method according to claim 6 wherein the synphysiodal joints are intervertebral joints.

8. A method according to claim 5 wherein the method is performed using endoscopic/arthroscopic surgical instrumentation and under fiberoptic visualization.

9. A method according to claim 8 wherein the instrumentation comprises a static mixer and delivery cannula to mix and deliver the composition.

10. A method according to claim 1 wherein the composition parts comprise: (1) a quasi-prepolymer component comprising the reaction product of one or more polyols and one or more isocyanates, and (2) a curative component comprising one or more polyols, one or more chain extenders, one or more catalysts, wherein the composition is sufficiently flowable to permit it to be delivered to the tissue site by minimally invasive means and there undergo complete cure in situ under physiologically acceptable conditions in order to provide a biocompatible material.

11. A method according to claim 10 wherein the curing composition provides a surface exotherm of between about 50 and about 80 C.

12. A method according to claim 10 wherein the quasi-prepolymer further comprises a reactive hydrophobic additive and the composition provides improved cure characteristics and cured properties as compared to a comparable composition lacking the reactive hydrophobic additive component.

13. A method according, to claim 12 wherein the reactive hydrophobic additive is selected from the group consisting of hydroxyl- or amine-terminated compounds selected from the group consisting of polybutadiene, polyisobutylene, silicones, polyisoprene, copolymers of butadiene with acryolnitrile, copolymers of butadiene with styrene, copolymers of isoprene with acrylonitrile, copolymers of isoprene with styrene, and mixtures thereof.

14. A method according to claim 10 wherein the polyols in each component independently comprise polyether polyols.

15. A method according to claim 14 wherein the polyether polyols independently comprise polytetramethylene oxides provided in the form of a blend of two or more different molecular weights selected from the group consisting of 250, 650, 1000, 1400, 2000, and 2900.

16. A method according to claim 10 wherein the chain extender consists essentially of linear chain extenders.

17. A method according to claim 16 wherein the linear chain extenders comprise 1,4-butanediol.

18. A method according to claim 14 wherein within the prepolymer the polyether component is selected from the group consisting of linear or branched polyols with polyether backbones of polyoxyethylene, polyoxypropylene, and polytetramethylene oxide (polyoxytetramethylene), and copolymers thereof, and wherein the composition further comprises a hydrophobic polymer additive selected from the group consisting of hydroxyl- or amine-terminated compounds selected from the group consisting of polybutadiene, polyisoprene, polyisobutylene, silicones, polyethylenepropylenediene, copolymers of butadiene with acryolnitrile, copolymers of butadiene with styrene, copolymers of isoprene with acrylonitrile, copolymers of isoprene with styrene, and mixtures thereof.

19. A method according to claim 18 wherein the improved cured properties include a hardness of about 60 Shore A to about 95 Shore A.

20. A method according to claim 18 wherein the isocyanate is present in excess in the prepolymer component and consists essentially of 4,4'-diphenylmethanediisocyanate (MDI).

21. A method according to claim 10 wherein the catalyst comprises a combination of tin catalyst and a tertiary amine.

22. A method according to claim 21 wherein the composition cures within on the order of 5 minutes or less.

23. A method according to claim 12 wherein wherein the improved cure characteristics include a significant reduction in the appearance of bubbles when cured in the presence of moisture.

24. A method according to claim 12 wherein the polyols in each component independently comprise polyether polyols selected from the group consisting of polytetramethylene oxides provided in the form of a blend of two or more different molecular weights selected from the group consisting of 250, 650, 1000, 1400, 2000, and 2900; the reactive hydrophobic additives comprise hydroxyl- or amine-terminated compounds selected from the group consisting of polybutadiene, polyisobutylene, silicones, polyisoprene, copolymers of butadiene with acryolnitrile, copolymers of butadiene with styrene, copolymers of isoprene with acrylonitrile, copolymers of isoprene with styrene, and mixtures thereof; the chain extender consists essentially of linear chain extender, and the isocyanates consist essentially of 4,4'-diphenylmethanediisocyanate (MDI).

* * * * *

UNITED STATES PATENT AND TRADEMARK OFFICE
CERTIFICATE OF CORRECTION

PATENT NO. : 6,306,177 B1 Page 1 of 1
DATED : October 23, 2001
INVENTOR(S) : Jeffrey C. Felt et al.

It is certified that error appears in the above-identified patent and that said Letters Patent is hereby corrected as shown below:

<u>Column 44,</u>
Line 47, after "--D412--" add the language -- and wherein the cured biomaterial provides an articulating joint surface --.

Signed and Sealed this

Third Day of June, 2003

JAMES E. ROGAN
*Director of the United States Patent and Trademark Office*